US011216480B2

(12) United States Patent
Öz et al.

(10) Patent No.: US 11,216,480 B2
(45) Date of Patent: Jan. 4, 2022

(54) SYSTEM AND METHOD FOR QUERYING DATA POINTS FROM GRAPH DATA STRUCTURES

(71) Applicant: Nuance Communications, Inc., Burlington, MA (US)

(72) Inventors: Mehmet Mert Öz, Baden (AT); Matthais Helletzgruber, Vienna (AT); Peter Ungar, Burlington, MA (US)

(73) Assignee: NUANCE COMMUNICATIONS, INC., Burlington, MA (US)

( * ) Notice: Subject to any disclaimer, the term of this patent is extended or adjusted under 35 U.S.C. 154(b) by 150 days.

(21) Appl. No.: 16/441,740

(22) Filed: Jun. 14, 2019

(65) Prior Publication Data

US 2020/0394184 A1    Dec. 17, 2020

(51) Int. Cl.

| | |
|---|---|
| *G06F 16/248* | (2019.01) |
| *G06F 16/901* | (2019.01) |
| *G06F 16/2455* | (2019.01) |
| *G06F 16/22* | (2019.01) |
| *G16H 10/60* | (2018.01) |
| *G06F 3/0482* | (2013.01) |

(Continued)

(52) U.S. Cl.
CPC .......... *G06F 16/248* (2019.01); *G06F 3/0482* (2013.01); *G06F 9/451* (2018.02); *G06F 16/2246* (2019.01); *G06F 16/2455* (2019.01); *G06F 16/9024* (2019.01); *G06F 40/174* (2020.01); *G16H 10/60* (2018.01)

(58) Field of Classification Search
CPC .... G16H 20/30; G16H 15/00; G06F 21/6218; G06F 16/95; G06F 16/3338; G06F 21/554; G06F 16/248; G06K 9/00456
See application file for complete search history.

(56) References Cited

U.S. PATENT DOCUMENTS

| | | |
|---|---|---|
| 5,805,747 A | 9/1998 | Bradford |
| 5,809,476 A | 9/1998 | Ryan |
| 5,940,118 A | 8/1999 | Van Schyndel |

(Continued)

FOREIGN PATENT DOCUMENTS

| | | |
|---|---|---|
| CN | 101790752 A | 7/2010 |
| CN | 106448722 A | 2/2017 |

(Continued)

OTHER PUBLICATIONS

Non-Final Office Action issued in related U.S. Appl. No. 16/271,616 dated Nov. 15, 2019.

(Continued)

*Primary Examiner* — Etienne P Leroux
(74) *Attorney, Agent, or Firm* — Brian J. Colandreo; Michael T. Abramson; Holland & Knight LLP

(57) ABSTRACT

A method, computer program product, and computing system includes generating a graph data structure including a plurality of data points. A query for the graph data structure may be received via a user interface. At least one data point from the plurality of data points may be identified, via the user interface, in the graph data structure based upon, at least in part, the query. A selection of a data point from the identified at least one data point may be received via the user interface. The selected data point may be provided to one or more electronic data sources.

21 Claims, 11 Drawing Sheets

(51) Int. Cl.
*G06F 9/451* (2018.01)
*G06F 40/174* (2020.01)

(56) References Cited

U.S. PATENT DOCUMENTS

| | | | |
|---|---|---|---|
| 5,970,455 | A | 10/1999 | Wilcox et al. |
| 5,970,457 | A | 10/1999 | Brant et al. |
| 6,031,526 | A | 2/2000 | Shipp |
| 6,266,635 | B1 | 7/2001 | Sneh |
| 6,332,122 | B1 | 12/2001 | Ortega et al. |
| 6,401,063 | B1 | 6/2002 | Hebert et al. |
| 6,405,165 | B1 | 6/2002 | Blum et al. |
| 6,434,520 | B1 | 8/2002 | Kanevsky et al. |
| 6,523,166 | B1 | 2/2003 | Mishra et al. |
| 6,589,169 | B1 | 7/2003 | Surwit et al. |
| 6,801,916 | B2 | 10/2004 | Roberge et al. |
| 6,823,203 | B2 | 11/2004 | Jordan |
| 6,847,336 | B1 | 1/2005 | Lemelson et al. |
| 6,915,254 | B1 | 7/2005 | Heinze et al. |
| 7,236,618 | B1 | 6/2007 | Chui et al. |
| 7,298,930 | B1 | 11/2007 | Erol et al. |
| 7,412,396 | B1 | 8/2008 | Haq |
| 7,493,253 | B1 | 2/2009 | Ceusters et al. |
| 7,496,500 | B2 | 2/2009 | Reed et al. |
| 7,516,070 | B2 | 4/2009 | Kahn |
| 7,558,156 | B2 | 7/2009 | Vook et al. |
| 7,817,805 | B1 | 10/2010 | Griffin |
| 7,830,962 | B1 | 11/2010 | Fernandez |
| 8,214,082 | B2 | 7/2012 | Tsai et al. |
| 8,345,887 | B1 | 1/2013 | Betbeder |
| 8,369,593 | B2 | 2/2013 | Peng et al. |
| 8,589,177 | B2 | 11/2013 | Haq |
| 8,589,372 | B2 | 11/2013 | Krislov |
| 8,606,594 | B2 | 12/2013 | Stem et al. |
| 8,661,012 | B1* | 2/2014 | Baker ............ G06F 16/3338 707/706 |
| 8,843,372 | B1 | 9/2014 | Isenberg |
| 8,983,889 | B1 | 3/2015 | Stoneman |
| 9,146,301 | B2 | 9/2015 | Adcock et al. |
| 9,224,180 | B2 | 12/2015 | Macoviak et al. |
| 9,270,964 | B1 | 2/2016 | Tseytlin |
| 9,293,151 | B2 | 3/2016 | Herbig et al. |
| 9,326,143 | B2 | 4/2016 | McFarland |
| 9,338,493 | B2 | 10/2016 | Van Os et al. |
| 9,536,049 | B2 | 1/2017 | Brown et al. |
| 9,536,106 | B2 | 1/2017 | Fram |
| 9,569,593 | B2 | 2/2017 | Casella dos Santos |
| 9,569,594 | B2 | 2/2017 | Casella dos Santos |
| 9,668,006 | B2 | 5/2017 | Betts et al. |
| 9,668,024 | B2 | 5/2017 | Os et al. |
| 9,668,066 | B1 | 5/2017 | Betts et al. |
| 9,679,102 | B2 | 6/2017 | Cardoza et al. |
| 9,779,631 | B1 | 10/2017 | Miller et al. |
| 9,785,753 | B2 | 10/2017 | Casella dos Santos |
| 9,799,206 | B1 | 10/2017 | Wilson Van Horn et al. |
| 9,824,691 | B1 | 11/2017 | Montero et al. |
| RE47,049 | E | 9/2018 | Zhu |
| 10,090,068 | B2 | 10/2018 | Kusens et al. |
| 10,219,083 | B2 | 2/2019 | Farmani et al. |
| 10,423,948 | B1 | 9/2019 | Wilson et al. |
| 10,440,498 | B1 | 10/2019 | Amengual Gari et al. |
| 10,491,598 | B2 | 11/2019 | Leblang et al. |
| 10,559,295 | B1 | 2/2020 | Abel |
| 10,693,872 | B1 | 6/2020 | Larson et al. |
| 10,785,565 | B2 | 9/2020 | Mate et al. |
| 10,810,574 | B1 | 10/2020 | Wilson et al. |
| 2001/0029322 | A1 | 10/2001 | Iliff |
| 2001/0041992 | A1 | 11/2001 | Lewis et al. |
| 2001/0042114 | A1 | 11/2001 | Agraharam et al. |
| 2002/0032583 | A1 | 3/2002 | Joao |
| 2002/0069056 | A1 | 6/2002 | Nofsinger |
| 2002/0072896 | A1 | 6/2002 | Roberge et al. |
| 2002/0082825 | A1 | 6/2002 | Rowlandson et al. |
| 2002/0143533 | A1 | 10/2002 | Lucas et al. |
| 2002/0170565 | A1 | 11/2002 | Walker et al. |
| 2002/0178002 | A1 | 11/2002 | Boguraev et al. |
| 2002/0194005 | A1 | 12/2002 | Lahr |
| 2003/0028401 | A1 | 2/2003 | Kaufman et al. |
| 2003/0105638 | A1 | 6/2003 | Taira |
| 2003/0125940 | A1 | 7/2003 | Basson et al. |
| 2003/0154085 | A1 | 8/2003 | Kelley |
| 2003/0185411 | A1 | 10/2003 | Atlas et al. |
| 2003/0216937 | A1 | 11/2003 | Schreiber et al. |
| 2004/0078228 | A1 | 4/2004 | Fitzgerald et al. |
| 2004/0122701 | A1 | 6/2004 | Dahlin |
| 2004/0128323 | A1 | 7/2004 | Walker |
| 2004/0162728 | A1 | 8/2004 | Thomson et al. |
| 2004/0167644 | A1 | 8/2004 | Swinney |
| 2004/0172070 | A1 | 9/2004 | Moore et al. |
| 2004/0186712 | A1 | 9/2004 | Coles et al. |
| 2004/0243545 | A1 | 12/2004 | Boone et al. |
| 2004/0247016 | A1 | 12/2004 | Faries, Jr. et al. |
| 2005/0055215 | A1 | 3/2005 | Klotz |
| 2005/0075543 | A1 | 4/2005 | Calabrese |
| 2005/0165285 | A1 | 7/2005 | Liff |
| 2005/0192848 | A1 | 9/2005 | Kozminski et al. |
| 2006/0041427 | A1 | 2/2006 | Yegnanarayanan et al. |
| 2006/0041428 | A1 | 2/2006 | Fritsch et al. |
| 2006/0074656 | A1 | 4/2006 | Mathias et al. |
| 2006/0092978 | A1 | 5/2006 | John et al. |
| 2006/0104454 | A1 | 5/2006 | Guitarte Perez et al. |
| 2006/0104458 | A1 | 5/2006 | Kenoyer et al. |
| 2006/0142739 | A1 | 6/2006 | DiSilestro et al. |
| 2006/0173753 | A1* | 8/2006 | Padmanabhan ......... G06F 16/95 705/7.32 |
| 2006/0241943 | A1 | 10/2006 | Benja-Athon et al. |
| 2006/0277071 | A1 | 12/2006 | Shufeldt |
| 2007/0033032 | A1 | 2/2007 | Schubert et al. |
| 2007/0071206 | A1 | 3/2007 | Gainsboro et al. |
| 2007/0136218 | A1 | 6/2007 | Bauer et al. |
| 2007/0167709 | A1 | 7/2007 | Slayton et al. |
| 2007/0169021 | A1 | 7/2007 | Huynh et al. |
| 2007/0208567 | A1 | 9/2007 | Amento et al. |
| 2007/0233488 | A1 | 10/2007 | Carus et al. |
| 2007/0260977 | A1 | 11/2007 | Allard et al. |
| 2008/0004505 | A1 | 1/2008 | Kapit et al. |
| 2008/0004904 | A1 | 1/2008 | Tran |
| 2008/0040162 | A1* | 2/2008 | Brice .................... G16H 15/00 705/3 |
| 2008/0059182 | A1 | 3/2008 | Benja-Athon et al. |
| 2008/0062280 | A1 | 3/2008 | Wang et al. |
| 2008/0071575 | A1 | 3/2008 | Climax et al. |
| 2008/0177537 | A1 | 7/2008 | Ash et al. |
| 2008/0240463 | A1 | 10/2008 | Florencio et al. |
| 2008/0247274 | A1 | 10/2008 | Seltzer et al. |
| 2008/0263451 | A1 | 10/2008 | Portele et al. |
| 2008/0285772 | A1 | 11/2008 | Haulick et al. |
| 2009/0024416 | A1 | 1/2009 | McLaughlin et al. |
| 2009/0055735 | A1 | 2/2009 | Zaleski et al. |
| 2009/0070103 | A1 | 3/2009 | Beggelman et al. |
| 2009/0089100 | A1 | 4/2009 | Nenov et al. |
| 2009/0136094 | A1 | 5/2009 | Driver |
| 2009/0150771 | A1 | 6/2009 | Buck et al. |
| 2009/0172773 | A1 | 7/2009 | Moore |
| 2009/0177477 | A1 | 7/2009 | Nenov et al. |
| 2009/0177492 | A1 | 7/2009 | Hasan et al. |
| 2009/0187407 | A1 | 7/2009 | Soble et al. |
| 2009/0198520 | A1 | 8/2009 | Piovanetti-Perez |
| 2009/0213123 | A1 | 8/2009 | Crow |
| 2009/0259136 | A1 | 10/2009 | Schieb |
| 2009/0270690 | A1 | 10/2009 | Roos et al. |
| 2010/0036676 | A1 | 2/2010 | Safdi et al. |
| 2010/0039296 | A1 | 2/2010 | Marggraff et al. |
| 2010/0076760 | A1 | 3/2010 | Kraenzel et al. |
| 2010/0076784 | A1 | 3/2010 | Greenburg et al. |
| 2010/0077289 | A1 | 3/2010 | Das et al. |
| 2010/0082657 | A1 | 4/2010 | Paprizos et al. |
| 2010/0088095 | A1 | 4/2010 | John |
| 2010/0094656 | A1 | 4/2010 | Conant |
| 2010/0094657 | A1 | 4/2010 | Stem et al. |
| 2010/0100376 | A1 | 4/2010 | Harrington |
| 2010/0131532 | A1 | 5/2010 | Schultz |
| 2010/0145736 | A1 | 6/2010 | Rohwer |
| 2010/0223216 | A1 | 9/2010 | Eggert et al. |

(56) References Cited

U.S. PATENT DOCUMENTS

| | | |
|---|---|---|
| 2010/0238323 A1 | 9/2010 | Englund |
| 2010/0241662 A1 | 9/2010 | Keith, Jr. |
| 2011/0015943 A1 | 1/2011 | Keldie et al. |
| 2011/0035221 A1 | 2/2011 | Zhang et al. |
| 2011/0063405 A1 | 3/2011 | Yam |
| 2011/0063429 A1 | 3/2011 | Contolini et al. |
| 2011/0066425 A1 | 3/2011 | Hudgins et al. |
| 2011/0071675 A1 | 3/2011 | Wells et al. |
| 2011/0096941 A1 | 4/2011 | Marzetta et al. |
| 2011/0119163 A1 | 5/2011 | Smith |
| 2011/0145013 A1 | 6/2011 | McLaughlin |
| 2011/0150420 A1 | 6/2011 | Cordonnier |
| 2011/0153520 A1 | 6/2011 | Coifman |
| 2011/0161113 A1 | 6/2011 | Rumak et al. |
| 2011/0166884 A1 | 7/2011 | Lesselroth |
| 2011/0178798 A1 | 7/2011 | Flaks et al. |
| 2011/0178813 A1 | 7/2011 | Moore |
| 2011/0202370 A1 | 8/2011 | Green, III et al. |
| 2011/0238435 A1 | 9/2011 | Rapaport |
| 2011/0246216 A1 | 10/2011 | Agrawal |
| 2011/0251852 A1 | 10/2011 | Bias |
| 2011/0286584 A1 | 11/2011 | Angel et al. |
| 2011/0301982 A1 | 12/2011 | Green, Jr. et al. |
| 2012/0020485 A1 | 1/2012 | Visser et al. |
| 2012/0029918 A1 | 2/2012 | Bachtiger |
| 2012/0053936 A1 | 3/2012 | Marvit |
| 2012/0076316 A1 | 3/2012 | Zhu et al. |
| 2012/0078626 A1 | 3/2012 | Tsai et al. |
| 2012/0101847 A1 | 4/2012 | Johnson et al. |
| 2012/0134507 A1 | 5/2012 | Dimitriadis et al. |
| 2012/0155703 A1 | 6/2012 | Hernandez-Abrego et al. |
| 2012/0158432 A1 | 6/2012 | Jain et al. |
| 2012/0159391 A1 | 6/2012 | Berry et al. |
| 2012/0173281 A1 | 7/2012 | DiLella et al. |
| 2012/0197660 A1 | 8/2012 | Prodanovich |
| 2012/0208166 A1 | 8/2012 | Ernst et al. |
| 2012/0212337 A1 | 8/2012 | Montyne et al. |
| 2012/0215551 A1 | 8/2012 | Flanagan et al. |
| 2012/0215557 A1 | 8/2012 | Flanagan et al. |
| 2012/0215559 A1 | 8/2012 | Flanagan et al. |
| 2012/0239430 A1 | 9/2012 | Corfield |
| 2012/0253801 A1 | 10/2012 | Santos-Lang et al. |
| 2012/0253811 A1 | 10/2012 | Breslin |
| 2012/0254917 A1 | 10/2012 | Burkitt et al. |
| 2012/0323574 A1 | 12/2012 | Wang et al. |
| 2012/0323575 A1 | 12/2012 | Gibbon et al. |
| 2012/0323589 A1 | 12/2012 | Udani |
| 2013/0017834 A1 | 1/2013 | Han et al. |
| 2013/0035961 A1 | 2/2013 | Yegnanarayanan |
| 2013/0041682 A1 | 2/2013 | Gottlieb et al. |
| 2013/0041685 A1 | 2/2013 | Yegnanarayanan |
| 2013/0064358 A1 | 3/2013 | Nusbaum |
| 2013/0073306 A1 | 3/2013 | Shlain et al. |
| 2013/0080879 A1 | 3/2013 | Darling |
| 2013/0103400 A1 | 4/2013 | Yegnanarayanan et al. |
| 2013/0138457 A1 | 5/2013 | Ragusa |
| 2013/0173287 A1 | 7/2013 | Cashman et al. |
| 2013/0188923 A1 | 7/2013 | Hartley et al. |
| 2013/0238312 A1 | 9/2013 | Waibel |
| 2013/0238329 A1 | 9/2013 | Casella dos Santos |
| 2013/0238330 A1 | 9/2013 | Casella dos Santos |
| 2013/0246098 A1 | 9/2013 | Habboush et al. |
| 2013/0246329 A1 | 9/2013 | Pasquero et al. |
| 2013/0297347 A1 | 11/2013 | Cardoza et al. |
| 2013/0297348 A1 | 11/2013 | Cardoza et al. |
| 2013/0301837 A1 | 11/2013 | Kim et al. |
| 2013/0332004 A1 | 12/2013 | Gompert et al. |
| 2013/0339030 A1 | 12/2013 | Ehsani et al. |
| 2014/0019128 A1 | 1/2014 | Riskin et al. |
| 2014/0035920 A1 | 2/2014 | Duwenhorst |
| 2014/0050307 A1 | 2/2014 | Yuzefovich |
| 2014/0073880 A1 | 3/2014 | Boucher |
| 2014/0074454 A1 | 3/2014 | Brown |
| 2014/0093135 A1 | 4/2014 | Reid et al. |
| 2014/0096091 A1 | 4/2014 | Reid et al. |
| 2014/0122109 A1 | 5/2014 | Ghanbari |
| 2014/0142944 A1 | 5/2014 | Ziv et al. |
| 2014/0164994 A1 | 6/2014 | Myslinski |
| 2014/0169767 A1 | 6/2014 | Goldberg |
| 2014/0188475 A1 | 7/2014 | Lev-Tov et al. |
| 2014/0207491 A1 | 7/2014 | Zimmerman et al. |
| 2014/0222526 A1 | 8/2014 | Shakil et al. |
| 2014/0223467 A1 | 8/2014 | Hayton et al. |
| 2014/0249818 A1 | 9/2014 | Yegnanarayanan et al. |
| 2014/0249830 A1 | 9/2014 | Gallopyn et al. |
| 2014/0249831 A1 | 9/2014 | Gallopyn et al. |
| 2014/0249847 A1 | 9/2014 | Soon-Shlong et al. |
| 2014/0278522 A1 | 9/2014 | Ramsey |
| 2014/0279893 A1 | 9/2014 | Branton |
| 2014/0281974 A1 | 9/2014 | Shi et al. |
| 2014/0288968 A1 | 9/2014 | Johnson |
| 2014/0306880 A1 | 10/2014 | Greif et al. |
| 2014/0324477 A1 | 10/2014 | Oez |
| 2014/0330586 A1 | 11/2014 | Riskin et al. |
| 2014/0337016 A1 | 11/2014 | Herbig et al. |
| 2014/0337048 A1 | 11/2014 | Brown et al. |
| 2014/0343939 A1 | 11/2014 | Mathias et al. |
| 2014/0362253 A1 | 12/2014 | Kim et al. |
| 2014/0365239 A1 | 12/2014 | Sadeghi |
| 2014/0365241 A1 | 12/2014 | Dillie et al. |
| 2014/0365242 A1 | 12/2014 | Neff |
| 2015/0046183 A1 | 2/2015 | Cireddu |
| 2015/0046189 A1 | 2/2015 | Dao |
| 2015/0052541 A1 | 2/2015 | Cheng |
| 2015/0070507 A1 | 3/2015 | Kagan |
| 2015/0086038 A1 | 3/2015 | Stein et al. |
| 2015/0088514 A1 | 3/2015 | Typrin |
| 2015/0088546 A1 | 3/2015 | Balram et al. |
| 2015/0120305 A1 | 4/2015 | Buck et al. |
| 2015/0120321 A1 | 4/2015 | David et al. |
| 2015/0124277 A1 | 5/2015 | Ono et al. |
| 2015/0124975 A1 | 5/2015 | Pontoppidan |
| 2015/0172262 A1 | 6/2015 | Ortiz, Jr. et al. |
| 2015/0172319 A1* | 6/2015 | Rodniansky ......... G06F 21/554 726/1 |
| 2015/0185312 A1 | 7/2015 | Gaubitch et al. |
| 2015/0187209 A1 | 7/2015 | Brandt |
| 2015/0278449 A1 | 10/2015 | Laborde |
| 2015/0278534 A1 | 10/2015 | Thiyagarajan et al. |
| 2015/0290802 A1 | 10/2015 | Buehler et al. |
| 2015/0294079 A1 | 10/2015 | Bergougnan |
| 2015/0294089 A1 | 10/2015 | Nichols |
| 2015/0302156 A1 | 10/2015 | Parsadoust |
| 2015/0310174 A1 | 10/2015 | Coudert et al. |
| 2015/0310362 A1 | 10/2015 | Huffman |
| 2015/0356250 A1 | 12/2015 | Polimeni |
| 2015/0379200 A1 | 12/2015 | Gifford et al. |
| 2015/0379209 A1 | 12/2015 | Kusuma et al. |
| 2016/0012198 A1 | 1/2016 | Gainer, III et al. |
| 2016/0034643 A1 | 2/2016 | Zasowski |
| 2016/0063206 A1 | 3/2016 | Wilson |
| 2016/0064000 A1 | 3/2016 | Mizumoto et al. |
| 2016/0098521 A1 | 4/2016 | Koziol |
| 2016/0119338 A1 | 4/2016 | Cheyer |
| 2016/0148077 A1 | 5/2016 | Cox et al. |
| 2016/0163331 A1 | 6/2016 | Yamaguchi |
| 2016/0165350 A1 | 6/2016 | Benattar |
| 2016/0174903 A1 | 6/2016 | Cutaia |
| 2016/0176375 A1 | 6/2016 | Bolton et al. |
| 2016/0179770 A1 | 6/2016 | Koll et al. |
| 2016/0188809 A1 | 6/2016 | Legorburn |
| 2016/0191357 A1 | 6/2016 | Orner et al. |
| 2016/0196821 A1 | 7/2016 | Yegnanarayanan et al. |
| 2016/0203327 A1* | 7/2016 | Akkiraju ............ G06F 21/6218 707/785 |
| 2016/0217807 A1 | 7/2016 | Gainsboro et al. |
| 2016/0234034 A1 | 8/2016 | Mahar et al. |
| 2016/0261930 A1 | 9/2016 | Kim |
| 2016/0275187 A1 | 9/2016 | Chowdhury et al. |
| 2016/0300020 A1 | 10/2016 | Wetta et al. |
| 2016/0342845 A1 | 11/2016 | Tien-Spalding et al. |
| 2016/0350950 A1 | 12/2016 | Ritchie et al. |
| 2016/0357538 A1 | 12/2016 | Lewallen et al. |
| 2016/0358632 A1 | 12/2016 | Lakhani et al. |

(56) References Cited

U.S. PATENT DOCUMENTS

| | | |
|---|---|---|
| 2016/0360336 A1 | 12/2016 | Gross et al. |
| 2016/0364606 A1 | 12/2016 | Conway et al. |
| 2017/0004260 A1 | 1/2017 | Moturu et al. |
| 2017/0011194 A1 | 1/2017 | Arshad et al. |
| 2017/0011740 A1 | 1/2017 | Gauci |
| 2017/0017834 A1 | 1/2017 | Sabitov et al. |
| 2017/0019744 A1 | 1/2017 | Matsumoto et al. |
| 2017/0046326 A1 | 2/2017 | Waibel |
| 2017/0069226 A1 | 3/2017 | Spinelli et al. |
| 2017/0076619 A1 | 3/2017 | Wallach et al. |
| 2017/0083214 A1 | 3/2017 | Furesjo et al. |
| 2017/0091246 A1 | 3/2017 | Risvik et al. |
| 2017/0093848 A1 | 3/2017 | Poisner et al. |
| 2017/0116384 A1 | 4/2017 | Ghani |
| 2017/0116392 A1 | 4/2017 | Casella Dos Santos |
| 2017/0131384 A1 | 5/2017 | Davis et al. |
| 2017/0178664 A1 | 6/2017 | Wingate et al. |
| 2017/0197636 A1 | 7/2017 | Beauvais |
| 2017/0228500 A1 | 8/2017 | Massengale |
| 2017/0242840 A1 | 8/2017 | Lu et al. |
| 2017/0316775 A1 | 11/2017 | Le et al. |
| 2017/0334069 A1 | 11/2017 | Wang et al. |
| 2018/0004915 A1 | 1/2018 | Talbot et al. |
| 2018/0025093 A1 | 1/2018 | Xia et al. |
| 2018/0032702 A1 | 2/2018 | Casella dos Santos |
| 2018/0060282 A1 | 3/2018 | Kaljurand |
| 2018/0075845 A1 | 3/2018 | Kochura |
| 2018/0081859 A1 | 3/2018 | Snider et al. |
| 2018/0107815 A1 | 4/2018 | Wu et al. |
| 2018/0122506 A1 | 5/2018 | Grantcharov et al. |
| 2018/0130554 A1 | 5/2018 | Cheng |
| 2018/0144120 A1 | 5/2018 | Fram |
| 2018/0144747 A1 | 5/2018 | Skarbovsky et al. |
| 2018/0156887 A1 | 6/2018 | Qiu et al. |
| 2018/0158461 A1 | 6/2018 | Wolff et al. |
| 2018/0158555 A1 | 6/2018 | Cashman et al. |
| 2018/0167243 A1 | 6/2018 | Gerdes |
| 2018/0181716 A1 | 6/2018 | Mander et al. |
| 2018/0197544 A1 | 7/2018 | Brooksby et al. |
| 2018/0197548 A1 | 7/2018 | Palakodety et al. |
| 2018/0218731 A1 | 8/2018 | Gustafson |
| 2018/0225277 A1 | 8/2018 | Alba |
| 2018/0232591 A1 | 8/2018 | Hicks et al. |
| 2018/0240538 A1 | 8/2018 | Koll et al. |
| 2018/0261307 A1 | 9/2018 | Couse et al. |
| 2018/0277017 A1 | 9/2018 | Cheung |
| 2018/0289291 A1 | 10/2018 | Richie |
| 2018/0310114 A1 | 10/2018 | Eronen et al. |
| 2018/0314689 A1 | 11/2018 | Wang et al. |
| 2018/0315428 A1 | 11/2018 | Johnson et al. |
| 2018/0336275 A1 | 11/2018 | Graham |
| 2019/0005959 A1 | 1/2019 | Cameron et al. |
| 2019/0012449 A1 | 1/2019 | Cheyer |
| 2019/0042606 A1 | 2/2019 | Griffith et al. |
| 2019/0051395 A1 | 2/2019 | Owen et al. |
| 2019/0096534 A1 | 3/2019 | Joao |
| 2019/0121532 A1 | 4/2019 | Strader et al. |
| 2019/0122766 A1 | 4/2019 | Strader et al. |
| 2019/0130073 A1 | 5/2019 | Sun et al. |
| 2019/0141031 A1 | 5/2019 | Devdas et al. |
| 2019/0172493 A1 | 6/2019 | Khan et al. |
| 2019/0182124 A1 | 6/2019 | Jeuk et al. |
| 2019/0214121 A1 | 7/2019 | O'Keeffe et al. |
| 2019/0246075 A1 | 8/2019 | Khadloya et al. |
| 2019/0251156 A1 | 8/2019 | Waibel |
| 2019/0265345 A1 | 8/2019 | Jungmaier et al. |
| 2019/0272844 A1 | 9/2019 | Sharma et al. |
| 2019/0313903 A1 | 10/2019 | McKinnon |
| 2020/0005939 A1* | 1/2020 | Stevens .......... G16H 20/30 |
| 2020/0034753 A1 | 1/2020 | Hammad |
| 2020/0279107 A1* | 9/2020 | Staar .......... G06K 9/00456 |

FOREIGN PATENT DOCUMENTS

| | | |
|---|---|---|
| EP | 1769771 A1 | 4/2007 |
| EP | 1927221 B1 | 11/2013 |
| JP | 2011182857 A | 9/2011 |
| JP | 2015533248 A | 11/2015 |
| KR | 20130118510 A1 | 10/2013 |
| WO | 0008585 A2 | 2/2000 |
| WO | 2013082087 A1 | 6/2013 |
| WO | 2014101472 A1 | 3/2014 |
| WO | 2013082087 A1 | 9/2014 |
| WO | 2014134089 A1 | 9/2014 |
| WO | 2016125053 A1 | 8/2016 |
| WO | 20160126813 A1 | 8/2016 |
| WO | 20160149794 A1 | 9/2016 |
| WO | 2017031972 A1 | 3/2017 |
| WO | 2017133934 A1 | 8/2017 |
| WO | 2019032778 A1 | 2/2019 |

OTHER PUBLICATIONS

Non-Final Office Action issued in related U.S. Appl. No. 16/192,358 dated Nov. 19, 2019.
Non-Final Office Action issued in related U.S. Appl. No. 16/059,944 dated Dec. 23, 2019.
Non-Final Office Action issued in related U.S. Appl. No. 16/059,818 dated Jan. 9, 2020.
Non-Final Office Action issued in related U.S. Appl. No. 16/058,912 dated Jan. 27, 2020.
Non-Final Office Action issued in related U.S. Appl. No. 16/292,920 dated Feb. 28, 2020.
Non-Final Office Action issued in related U.S. Appl. No. 16/100,030, dated Mar. 4, 2020.
Notice of Allowance issued in related U.S. Appl. No. 16/271,616, dated Mar. 17, 2019.
Dibiase, J. H. et al., "Robust Localization in Reverberant Rooms," in Microphone Arrays—Signal Processing Techniques and Applications, Ch. 8, pp. 157-180.
Valin, Jean-Marc et al., "Robust Sound Source Localization Using a Microphone Array on a Mobile Robot," Proceedings of the 2003 IEEE/RSJ International Conference on Intelligent Robots and Systems, vol. 2, 2003, pp. 1228-1233.
Wang, L. et al., "Over-determined Source Separation and Localization Using Distributed Microphone," IEEE/ACM Transactions on Audio, Speech, and Language Processing, vol. 24, No. 9, Sep. 2016, pp. 1573-1588.
Notice of Allowance issued in related U.S. Appl. No. 16/108,959, dated Nov. 6, 2019.
Bahdanau, D. et al., "Neural Machine Translation by Jointly Learning to Align and Translate", Published as a Conference Paper at ICLR 2015, May 19, 2016, 15 pages.
Final Office Action issued in related U.S. Appl. No. 16/192,427, dated Mar. 6, 2020.
Final Office Action issued in related U.S. Appl. No. 16/058,871, dated Mar. 19, 2020.
Final Office Action issued in related U.S. Appl. No. 16/059,944, dated Mar. 26, 2020.
Non-Final Office Action issued in related U.S. Appl. No. 16/058,936, dated Apr. 15, 2020.
Non-Final Office Action issued in related U.S. Appl. No. 16/058,941, dated Apr. 15, 2020.
Non-Final Office Action issued in related U.S. Appl. No. 16/059,895, dated Apr. 24, 2020.
Non-Final Office Action issued in related U.S. Appl. No. 16/059,974, dated Apr. 24, 2020.
Non-Final Office Action issued in related U.S. Appl. No. 16/059,986, dated Apr. 24, 2020.
Final Office Action issued in related U.S. Appl. No. 16/100,310, dated May 8, 2020.
Final Office Action issued in related U.S. Appl. No. 16/058,912 dated May 26, 2020.
Non-Final Office Action issued in related U.S. Appl. No. 16/271,616, dated May 29, 2020.

(56) References Cited

OTHER PUBLICATIONS

Final Office Action issued in related U.S. Appl. No. 16/192,358, dated Jun. 2, 2020.
Non-Final Office Action issued in related U.S. Appl. No. 16/292,895, dated Jun. 5, 2020.
Final Office Action issued in related U.S. Appl. No. 16/058,941 dated Jun. 23, 2020.
Final Office Action issued in related U.S. Appl. No. 16/058,936 dated Jun. 23, 2020.
Non-Final Office Action issued in related U.S. Appl. No. 16/058,856 dated Jul. 2, 2020.
Final Office Action issued in related U.S. Appl. No. 16/059,986 dated Jul. 6, 2020.
Final Office Action issued in related U.S. Appl. No. 16/059,974 dated Jul. 6, 2020.
Final Office Action issued in related U.S. Appl. No. 16/059,895 dated Jul. 6, 2020.
Non-Final Office Action issued in related U.S. Appl. No. 16/059,944 dated Jul. 13, 2020.
Notice of Allowance issued in related U.S. Appl. No. 16/271,616 dated Jul. 13, 2020.
Non-Final Office Action issued in related U.S. Appl. No. 16/058,826 dated Jul. 17, 2020.
Non-Final Office Action issued in related U.S. Appl. No. 16/058,914 dated Jul. 17, 2020.
Non-Final Office Action issued in related U.S. Appl. No. 16/058,925 dated Jul. 20, 2020.
Non-Final Office Action issued in related U.S. Appl. No. 16/058,894 dated Jul. 30, 2020.
Non-Final Office Action issued in related U.S. Appl. No. 16/292,877 dated Jul. 23, 2020.
Non-Final Office Action issued in related U.S. Appl. No. 16/058,883 dated Jul. 31, 2020.
Non-Final Office Action issued in related U.S. Appl. No. 16/058,829 dated Aug. 5, 2020.
Final Office Action issued in related U.S. Appl. No. 16/058,856 dated Aug. 12, 2020.
Final Office Action issued in related U.S. Appl. No. 16/292,920 dated Aug. 11, 2020.
Non-Final Office Action issued in related U.S. Appl. No. 16/058,912 dated Aug. 20, 2020.
Non-Final Office Action issued in related U.S. Appl. No. 16/100,030 dated Aug. 25, 2020.
Lenert et al., "Design and Evaluation of a Wireless Electronic Health Records System for Field Care in Mass Casualty Settings", Journal of the American Medical Informatics Association, Nov. 2011-Dec. 18(6); pp. 842-852. shttps://www. ncbi.nim.nih.gov/pmc/articles/PMC3198000/>.
International Search Report issued in PCT Application Serial No. PCT/US2019/020742 dated May 14, 2019.
International Search Report issued in PCT Application Serial No. PCT/US2019/020739 dated May 17, 2019.
International Search Report issued in PCT Application Serial No. PCT/US2019/020763 dated May 23, 2019.
International Search Report issued in PCT Application Serial No. PCT/US2019/020765 dated May 23, 2019.
International Search Report issued in PCT Application Serial No. PCT/US2019/020778 dated May 23, 2019.
International Search Report issued in PCT Application Serial No. PCT/US2019/020771 dated May 30, 2019.
Non-Final Office Action issued in U.S. Appl. No. 16/059,818 dated Jun. 10, 2019.
International Search Report issued in PCT Application Serial No. PCT/US2019/020721 dated Jun. 6, 2019.
International Search Report issued in PCT Application Serial No. PCT/US2019/020755 dated Jun. 6, 2019.
Final Office Action issued in U.S. Appl. No. 16/059,967 dated Jul. 11, 2019.
Final Office Action issued in U.S. Appl. No. 16/100,030 dated Jul. 18, 2019.
Notice of Allowance issued in U.S. Appl. No. 16/100,030 dated Oct. 9, 2019.
Non-Final Office Action issued in U.S. Appl. No. 16/192,427 dated Oct. 3, 2019.
Non-Final Office Action issued in U.S. Appl. No. 16/058,951 dated Jul. 25, 2019.
International Search Report issued in International App. No. PCT/US2019/020738 dated Jul. 17, 2019.
Final Office Action issued in U.S. Appl. No. 16/058,912 dated Jul. 31, 2019.
Final Office Action issued in U.S. Appl. No. 16/059,944 dated Aug. 22, 2019.
Non-Final Office Action issued in U.S. Appl. No. 16/058,871 dated Sep. 23, 2019.
Final Office Action issued in U.S. Appl. No. 16/059,818 dated Sep. 25, 2019.
Non-Final Office Action issued in U.S. Appl. No. 16/059,944 dated Sep. 28, 2018.
International Search Report and Written Opinion issued in counterpart International Application Serial No. PCT/US2018/045923 dated Oct. 2, 2018.
International Search Report and Written Opinion dated Oct. 3, 2018 in counterpart International Application Serial No. PCT/US2018/046024.
International Search Report and Written Opinion dated Oct. 3, 2013 in counterpart International Application Serial No. PCT/US2018/045982.
International Search Report and Written Opinion dated Oct. 3, 2018 in counterpart International Application Serial No. PCT/US2018/046008.
International Search Report and Written Opinion dated Oct. 2, 2018 in counterpart International Application Serial No. PCT/US2018/046034.
International Search Report and Written Opinion dated Oct. 3, 2018 in counterpart International Application Serial No. PC/US2018/045926.
International Search Report and Written Opinion dated Sep. 21, 2018 in counterpart International Application Serial No. PCT/US2018/046002.
Non-Final Office Action dated in U.S. Appl. No. 16/059,818 dated Nov. 2, 2018.
International Search Report and Written Opinion dated Oct. 24, 2018 in counterpart International Application Serial No. PCT/US2018/046041.
International Search Report and Written Opinion dated Oct. 16, 2018 in counterpart International Application Serial No. PCT/US2018/046029.
International Search Report and Written Opinion dated Oct. 11, 2018 in counterpart International Application Serial No. PCT/US2018/045994.
International Search Report and Written Opinion dated Oct. 22, 2018 in counterpart International Application Serial No. PCT/US2018/045903.
International Search Report and Written Opinion dated Oct. 22, 2018 in PCT Application Serial No. PCT/US2018/045917.
Jeffrey Klann et el., "An Intelligent Listening Framework for Capturing Encounter Notes from a Doctor-Patient Dialog", BMC Med Inform Decis Mak. 2009; 9(Suppl 1): S3, Published online Nov. 3, 2009. doi: 10.1186/1472-6947-9-S1-S3, 5 pages.
Non-Final Office Action issued in U.S. Appl. No. 16/058,871 dated Dec. 3, 2018.
International Search Report issued in PCT Application Serial No. PCT/US2018/045971 dated Oct. 30, 2018.
International Search Report issued in PCT Application Serial No. PCT/US2018/046049 dated Nov. 2, 2018.
International Search Report issued in PCT Application Serial No. PCT/US2018/045921 dated Oct. 16, 2018.
International Search Report issued in PCT Application Serial No. PCT/US2018/045896 dated Oct. 17, 2018.
Non-Final Office Action issued in U.S. Appl. No. 16/059,967 dated Jan. 2, 2019.
Non-Final Office Action issued in U.S. Appl. No. 16/058,951 dated Oct. 5, 2018.

(56) References Cited

OTHER PUBLICATIONS

A Study of Vision based Human Motion Recognition and Analysis to Kale et al., Dec. 2016.
International Search Report issued in PCT Application Serial No. PCT/US2018/045908 dated Oct. 19, 2018.
International Search Report issued in PCT Application Serial No. PCT/US2018/045936 dated Oct. 18, 2018.
International Search Report issued in PCT Application Serial No. PCT/US2018/045987 dated Oct. 12, 2018.
International Search Report issued in PCT Application Serial No. PCT/US2018/046006 dated Oct. 15, 2018.
Invitation to Pay Additional Fees and, Where Applicable, Protest Fee issued in PCT Application Serial No. PCT/US2012/072041 dated Jun. 6, 2013.
International Search Report issued in PCT Application Serial No. PCT/US2012/072041 dated Aug. 2, 2013.
Alapetite et al., "introducing vocal modality into electronics anaesthesia record systems: possible effects on work practices in the operating room", EACE '05 Proceedings of the 2005 Annual Conference on European Association of Cognitive Ergonomics, Jan. 1, 2005, 197-204.
Alapetite, "Speech recognition for the anaesthesia record during crisis scenarios", 2008, International Journal of Medical Informatics, 2008, 77(1), 448-460.
Cimiano et al., "Learning concept hierarchies from text with a guided hierarchical clustering algorithm", in C. Biemann and G. Paas (eds.), Proceedings of the ICML 2005 Workshop on Learning and Extending Lexical Ontologies with Machine Learning Methods, Bonn Germany, 2005.
Fan et al., "Prismatic: Inducing Knowledge from a Large Scale Lexicalized Relation Resource", Proceedings of the NAACL HLT 2010 First Interational Workshop on Formalisms and Methodology for Learning by Reading, pp. 122-127, Los Angeles, California, Jun. 2010.
Florian et al., "A Statistical Model for Multilingual Entity Detection and Tracking", Proceedings of the Human Language Technologies Conference 2004.
Gomez-Perez et al., "An overview of methods and tools for ontology learning from texts", Knowledge Engineering Review 19:3, pp. 187-212, 2004.
Grasso et al., "Automated Speech Recognition in Medical Applications", MD Computing, 1995, pp. 16-23.
Harris, "Building a Large-scale Commerical NLG System for an EMR", Proceedings of the Fifth International Natural Language Generation Conference, pp. 157-160, 2008.
Jungk et al., "A Case Study in Designing Speech Interaction with a Patient Monitor", J Clinical Monitoring and Computing, 2000, 295-307.
Klann et al., "An Intelligent listening framework for capturing encounter notes from a doctor-patient dialog", BMC Medical Informatics and Decision Making 2009, published Nov. 3, 2009.
Meng et al., Generating Models of Surgical Procedures using UMLS Concepts and Multiple Sequence Alignment, AMIA Annual Symposium Proceedings, 2005, pp. 520-524.
MIT Computer Science and Artificial Intelligence Laboratory (CSAIL) Clinical Decision Making Group, "Fair Witness Capturing Patient-Provider Encounter through Text, Speech, and Dialogue Processing", Last updated on Apr. 9, 2010, http://groups.csail.mit.edu/medg/projects/fw.
Welty et al., "Large Scale Relation Detection", Proceedings of the NAACL HLT 2010 First International Workshop on Formalisms and Methodology for Learning by Reading, pp. 24-33, Jun. 2010.
Zafar et., "Continuous Speech Recognition for Clinicials", J Am Med Infor Assoc, 1999, pp. 195-204.
Final Office Action issued in U.S. Appl. No. 16/059,818 dated Feb. 28, 2019.
Non-Final Office Action issued in U.S. Appl. No. 16/100,030 dated Feb. 28, 2019.
Non-Final Office Action issued in U.S. Appl. No. 16/058,912 dated Mar. 6, 2019.
Final Office Action issued in U.S. Appl. No. 16/058,951 dated Apr. 4, 2019.
Final Office Action issued in U.S. Appl. No. 16/058,871 dated Apr. 8, 2019.
Non-Final Office Action issued in U.S. Appl. No. 16/059,944 dated Apr. 15, 2019.
International Search Report issued in PCT Application Serial No. PCT/US2019/020746 dated May 14, 2019.
Final Office Action issued in related U.S. Appl. No. 16/059,895 dated Mar. 24, 2021.
Final Office Action issued in related U.S. Appl. No. 16/059,986 dated Mar. 24, 2021.
Non-Final Office Action issued in related U.S. Appl. No. 16/292,895 dated Mar. 25, 2021.
Non-Final Office Action issued in related U.S. Appl. No. 16/292,920 dated Mar. 26, 2021.
Non-Final Office Action issued in related U.S. Appl. No. 16/270,888 dated Mar. 26, 2021.
Non-Final Office Action issued in related U.S. Appl. No. 16/271,329 dated Mar. 26, 2021.
Hu et al., "Deep Multimodel Speaker Naming", Computing Research Repository, vol. abs/1507.04831, 2015 (Year 2015).
Final Office Action issued in related U.S. Appl. No. 16/271,029 dated Apr. 1, 2021.
Non-Final Office Action issued in related U.S. Appl. No. 16/058,826 dated Apr. 6, 2021.
Notice of Allowance issued in related U.S. Appl. No. 16/058,871 dated Apr. 9, 2021.
Final Office Action issued in related U.S. Appl. No. 17/084,310 dated Apr. 12, 2021.
Non-Final Office Action issued in related U.S. Appl. No. 16/441,777 dated Feb. 4, 2021.
Non-Final Office Action issued in related U.S. Appl. No. 16/442,247 dated Apr. 15, 2021.
Non-Final Office Action issued in related U.S. Appl. No. 16/058,925 dated Apr. 16, 2021.
Non-Final Office Action issued in related U.S. Appl. No. 16/058,914 dated Apr. 16, 2021.
Non-Final Office Action issued in related U.S. Appl. No. 16/058,894 dated Apr. 16, 2021.
Supplementary European Search Report issued in counterpart Application Serial No. 188344752.8 dated Mar. 3, 2021.
Non-Final Office Action issued in related U.S. Appl. No. 16/058,883 dated Apr. 28, 2021.
Notice of Allowance issued in related U.S. Appl. No. 16/059,944 dated Apr. 30, 2021.
Final Office Action issued in related U.S. Appl. No. 16/270,782 dated May 7, 2021.
Notice of Allowance issued in related U.S. Appl. No. 16/441,777 dated May 14, 2021.
Final Office Action issued in related U.S. Appl. No. 17/084,448 dated Jun. 1, 2021.
Non-Final Office Action issued in related U.S. Appl. No. 16/292,893 dated Jun. 9, 2021.
David, G. C., Garcia, A. C., Rawls, A. W., & Chand, D. (2009). Listening to what is said—transcribing what is heard: the impact of speech recognition technology (SRT) on the practice of medical transcription (MT). Sociology of Health & Illness, 31 (6), 924-938. (Year: 2009).
Notice of Allowance issued in related U.S. Appl. No. 16/058,871 dated Jun. 14, 2021.
Non-Final Office Action issued in related U.S. Appl. No. 16/293,032 dated Jun. 24, 2021.
Non-Final Office Action issued in related U.S. Appl. No. 16/058,803 dated Jun. 24, 2021.
Non-Final Office Action issued in related U.S. Appl. No. 16/058,829 dated Jun. 25, 2021.
Final Office Action issued in related U.S. Appl. No. 16/192,358 dated Jun. 25, 2021.
Notice of Allowance issued in related U.S. Appl. No. 16/059,818 dated Jul. 2, 2021.
Notice of Allowance issued in related U.S. Appl. No. 16/058,936 dated Jul. 7, 2021.

(56) References Cited

OTHER PUBLICATIONS

Notice of Allowance issued in related U.S. Appl. No. 17/084,310 dated Jul. 9, 2021.
Notice of Allowance issued in related U.S. Appl. No. 16/058,941 dated Jul. 14, 2021.
Non-Final Office Action issued in related U.S. Appl. No. 16/059,818 dated Aug. 25, 2020.
Non-Final Office Action issued in related U.S. Appl. No. 16/058,803 dated Sep. 3, 2020.
YouTube video clip entitled "Nuance PowerMic Mobile gives clinicians greater mobility", retrieved from Internet: https://www.youtube.com/watch?v=OjqiePRFti@feature=emb-logo (Year: 2015), 3 pages.
Non-Final Office Action issued in related U.S. Appl. No. 16/271,029 dated Sep. 8, 2020.
Non-Final Office Action issued in related U.S. Appl. No. 16/293,032 dated Sep. 16, 2020.
Non-Final Office Action issued in related U.S. Appl. No. 16/192,427 dated Sep. 21, 2020.
Non-Final Office Action issued in related U.S. Appl. No. 16/292,893 dated Oct. 2, 2020.
David, G. C. et al., "Listening to what is said-transcribing what is heard: the impact of speech recognition technology (SRT) on the practice of medical transcription (MT)", Sociology of Heath and Illness, vol. 31, No. 6, pp. 924-938, (2009).
Non-Final Office Action issued in related U.S. Appl. No. 16/058,871 dated Oct. 5, 2020.
Non-Final Office Action issued in related U.S. Appl. No. 16/058,941 dated Oct. 26, 2020.
Non-Final Office Action issued in related U.S. Appl. No. 16/058,936 dated Oct. 26, 2020.
International Search Report and Written Opinion dated Aug. 19, 2020 in PCT Application Serial No. PCT/US2020/037284.
Final Office Action issued in related U.S. Appl. No. 16/058,826, dated Nov. 30, 2020.
Final Office Action issued in related U.S. Appl. No. 16/058,803 dated Nov. 30, 2020.
Final Office Action issued in related U.S. Appl. No. 16/058,883 dated Nov. 30, 2020.
Final Office Action issued in related U.S. Appl. No. 16/058,925 dated Nov. 30, 2020.
Final Office Action issued in related U.S. Appl. No. 16/058,914, dated Nov. 30, 2020.
Final Office Action issued in related U.S. Appl. No. 16/292,895, dated Nov. 30, 2020.
Non-Final Office Action issued in related U.S. Appl. No. 16/192,358, dated Nov. 27, 2020.
Final Office Action issued in related U.S. Appl. No. 16/059,818 dated Dec. 4, 2020.
Non-Final Office Action issued in related U.S. Appl. No. 16/059,895, dated Dec. 9, 2020.
Final Office Action issued in related U.S. Appl. No. 17/084,310 dated Dec. 22, 2020.
Non-Final Office Action issued in related U.S. Appl. No. 16/059,974, dated Dec. 18, 2020.
Non-Final Office Action issued in related U.S. Appl. No. 16/059,986, dated Dec. 18, 2020.
International Search Report and Written Opinion dated Aug. 31, 2020 in PCT Application Serial No. PCT/US2020/037226.
Final Office Action issued in related U.S. Appl. No. 16/058,829 dated Jan. 11, 2021.
Non-Final Office Action issued in related U.S. Appl. No. 17/084,310, dated Dec. 21, 2020.
Notice of Allowance issued in related U.S. Appl. No. 16/100,030 dated Jan. 11, 2021.
Angles, R., "A Comparison of Current Graph Database Models", In: 2012 IEEE 28th International Conference on Data Engineering Workshops, Apr. 5, 2012 (Apr. 5, 2012) Retrieved on Aug. 5, 2020 (Aug. 5, 2020) from URL:https://ieeexplore.ieee.org/document/6313676 entire document, 7 pages.
Final Office Action issued in related U.S. Appl. No. 16/059,944 dated Dec. 28, 2020.
Final Office Action issued in related U.S. Appl. No. 16/058,894 dated Dec. 1, 2020.
Final Office Action issued in related U.S. Appl. No. 16/058,941 dated Dec. 22, 2020.
Notice of Allowance issued in related U.S. Appl. No. 16/058,856 dated Jan. 19, 2021.
Non-Final Office Action issued in related U.S. Appl. No. 16/270,782 dated Jan. 19, 2021.
Notice of Allowance issued in related U.S. Appl. No. 16/058,912 dated Jan. 22, 2021.
Final Office Action issued in related U.S. Appl. No. 16/292,893 dated Jan. 28, 2021.
Notice of Allowance issued in related U.S. Appl. No. 16/100,030 dated Jan. 28, 2021.
Final Office Action issued in related U.S. Appl. No. 16/292,877 dated Feb. 8, 2021.
Non-Final Office Action issued in related U.S. Appl. No. 17/084,448 dated Feb. 10, 2021.
Non-Final Office Action issued in related U.S. Appl. No. 16/292,973 dated Feb. 12, 2021.
Final Office Action issued in related U.S. Appl. No. 16/192,427 dated Feb. 22, 2021.
International Search Report and Written Opinion dated Jan. 11, 2021 in PCT Application Serial No. PCT/US2020/053504.
International Search Report and Written Opinion dated Nov. 15, 2019 in PCT Application Serial No. PCT/US2019/047689.
Final Office Action issued in related U.S. Appl. No. 16/293,032 dated Mar. 1, 2021.
Non-Final Office Action issued in related U.S. Appl. No. 16/270,888 dated Mar. 2, 2021.
Notice of Allowance issued in related U.S. Appl. No. 16/058,856 dated Mar. 9, 2021.
Final Office Action issued in related U.S. Appl. No. 16/058,871, dated Mar. 18, 2021.
Non-Final Office Action issued in related U.S. Appl. No. 16/059,818 dated Mar. 18, 2021.
Zhou et al., "Applying the Narve Bayes Classifier to Assist Users in Detecting Speech Recognition Errors," Proceedings of the 38th Annual Hawaii International Conference on System Sciences, Big Island, HI, USA, 2005, pp. 183b-183b, doi: 10.1109/HICSS.2005.99.
Abdulkader et al., "Low Cost Correction of OCR Errors Using Learning in a Multi-Engine Environment," 2009 10th International Conference on Document Analysis and Recognition, Barcelona, 2009, pp. 576-580, doi: 10.1109/ICDAR.2009.242.
Notice of Allowance issued in related U.S. Appl. No. 16/292,920 dated Jul. 15, 2021.
Non-Final Office Action issued in related U.S. Appl. No. 16/773,447 dated Jul. 20, 2021.
Notice of Allowance issued in related U.S. Appl. No. 16/442,247 dated Jul. 22, 2021.
Communication issuing supplementary European Search Report of May 14, 2021 and Extended European Search Report dated Apr. 16, 2021 in counterpart Application Serial No. EP 18844226.3.
Communication issuing supplementary European Search Report of Apr. 8, 2021 and Extended European Search Report dated Mar. 10, 2021 in counterpart Application Serial No. EP 18845046.4.
YouTube video clip entitled "Nuance PowerMic Mobile gives clinicians greater mobility", retrieved from Internet: https://www.youtube.com/watch?v=OjqiePRFtl@feature=emb-logo (Year: 2015), 3 pages.
Gross R, et al.: "Towards a multimodal meeting record", Multimedia and Expo, 2000. ICME 2000. 2000 IEEE International Conference in New York, NY, USA 30 Jul. 2-Aug. 2, 2000, Piscataway, NJ, USA, IEEE, US, vol. 3, Jul. 30, 2000 (Jul. 30, 2000_, pp. 1593-1596, XP010512812, DOI: 10.1109/ICME.2000.871074 ISBN: 978-0-7803-6536-0 *the whole document*.
Communication issuing supplementary European Search Report of Apr. 8, 2021 and Extended European Search Report dated in Mar. 10, 2021 counterpart Application Serial No. EP 18842996.3.

(56) References Cited

OTHER PUBLICATIONS

Communication issuing supplementary European Search Report of May 19, 2021 and Extended European Search Report dated Apr. 19, 2021 in counterpart Application Serial No. EP 18844530.8.
Communication issuing supplementary European Search Report of May 19, 2021 and Extended Europe Search Report dated Apr. 19, 2021 in counterpart Application Serial No. EP 18843844.1.
Nadir, Weibel, et al.: "LAB-IN-A-BOX: semi-automatic tracking of activity in the medical office", Personal and Ubiqitous Computing, Springer Verlag, Lond, GB, vol. 19, No. 2, Sep. 28, 2014 (Sep. 28, 2014) pp. 317-334, XP058066121, ISSN: 1617-4909, DOI: 10.1007/S00779-014-0821-0 *abstract* *Section 4, The LAB-IN-A-BOX; p. 321-p. 327* *Section 5.2, "Data collection and analysis"; p. 330-p. 331* *table 1* *figures 7,8*.
Communication issuing supplementary European Search Report of May 28, 2021 and Extended European Search Report dated May 3, 2021 in counterpart Application Serial No. EP 18843648.9.
Communication issuing supplementary European Search Report of May 28, 2021 and Extended European Search Report dated Apr. 16, 2021 in counterpart Application Serial No. EP 18843945.9.
Communication issuing supplementary European Search Report of May 19, 2021 and Extended European Search Report dated Apr. 19, 2021 in counterpart Application Serial No. EP 18844669.4.
Yang, et al., "The Design and Implementation of a Smart e-Receptionist", IEE Potentials, IEEE, New York, NY, US, vo. 32, No. 4, Jul. 22, 2013 (Jul. 22, 2013), pp. 22-27, XP011522905, IsSSN: 0278-6648, DOI: 10.1109/MPOT.2012.2213851 *the whole document*.
Communication issuing supplementary European Search Report of May 14, 2021 and Extended European Search Report dated Apr. 16, 2021 in counterpart Application Serial No. EP 18843175.3.
Communication issuing supplementary European Search Report of May 28, 2021 and Extended European Search Report dated Apr. 29, 2021 in counterpart Application Serial No. EP 18845144.7.
Non-Final Office Action issued dated Aug. 6, 2021 in counterpart U.S. Appl. No. 16/270,782.
Final Office Action dated Aug. 19, 2021 in counterpart U.S. Appl. No. 16/292,973.
Final Office Action issued on Aug. 19, 2021 in counterpart U.S. Appl. No. 16/292,973.
Communication issuing supplementary European Search Report of Apr. 12, 2021 and Extended European Search Report of Mar. 12, 2021 in counterpart Application Serial No. EP 18843255.3.
Communication issuing supplementary European Search Report of May 26, 2021 and Extended European Search Report of Apr. 30, 2021 in counterpart Application Serial No. EP 18844675.1.
Communication issuing supplementary European Search Report of Mar. 30, 2021 and Extended European Search Report of Mar. 3, 2021 in counterpart Application Serial No. EP 18844752.8.
Shivappa, S. et al., "Role of Head Pse Estimation in Speech Acquisition from Distant Microphones," Acoustics, Speech and Signal Processing, ICASSP 2009, IEEE International Conference on IEEE, pp. 3557-3560, Apr. 19, 2009.
Communication issuing supplementary European Search Report of Apr. 6, 2021 and Extended European Search Report dated Mar. 8, 2021 in counterpart Application Serial No. EP 18844407.9.
Communication issuing supplementary European Search Report of Apr. 12, 2021 and Extended European Search Report of Apr. 19, 2021 in counterpart Application Serial No. EP 18843873.3.
Communication issuing supplementary European Search Report of Apr. 12, 2021 and Extended European Search Report of Mar. 11, 2021 in counterpart Application Serial No. EP 18843329.6.
Communication issuing supplementary European Search Report of Apr. 13, 2021 and Extended European Search Report of Apr. 19, 2021 in counterpart Application Serial No. EP 18843586.1.
Communication issuing supplementary European Search Report of Apr. 16, 2021 and Extended European Search Report of Mar. 22, 2021 in counterpart Application Serial No. EP 18843254.6.
Communication issuing supplementary European Search Report of May 26, 2021 and Extended European Search Report of Apr. 30, 2021 in counterpart Application Serial No. EP 18844406.1.
Non-Final Office Action issued in counterpart U.S. Appl. No. 16/271,029 dated Sep. 15, 2021.
Notice of Allowance issued in counterpart U.S. Appl. No. 16/059,895 dated Sep. 13, 2021.
Final Office Action issued in counterpart U.S. Appl. No. 16/270,888 dated Sep. 9, 2021.
Notice of Allowance issued in counterpart U.S. Appl. No. 17/084,448 dated Sep. 22, 2021.
Non-Final Office Action issued in counterpart U.S. Appl. No. 16/059,967 dated Sep. 20, 2021.
Klaan et al. , "An Intelligent listening framework for capturing encounter notes from a doctor-patient dialog," BMC Medical Informatics and Decision Making, vol. 9, Suppl, Suppl 1, S3. Nov. 2009.
Final Office Action issued in counterpart U.S. Appl. No. 16/292,895 dated Sep. 30, 2021.
Notice of Allowance issued in counterpart U.S. Appl. No. 16/059,974 dated Oct. 5, 2021.
Notice of Allowance issued in counterpart U.S. Appl. No. 16/059,986 dated Oct. 12, 2021.
Final Office Action issued in counterpart U.S. Appl. No. 16/058,826 dated Oct. 21, 2021.
Final Office Action issued in counterpart U.S. Appl. No. 16/058,894 dated Oct. 29, 2021.
Final Office Action issued in counterpart U.S. Appl. No. 16/058,883 dated Oct. 29, 2021.
Final Office Action issued in counterpart U.S. Appl. No. 16/058,925 dated Oct. 29, 2021.
Final Office Action issued in counterpart U.S. Appl. No. 16/058,914 dated Oct. 29, 2021.
Unknown, You Tube video clip entitled "Nuance Healthcare Florence Workflow Concept with Samsung Smartwatch Demo English," retrieved from Internet: https://www.youtube.com/watch?v=1-NVD60oyn) (Year: 2015).
Notice of Allowance issued in counterpart U.S. Appl. No. 16/038,886 dated Nov. 4, 2021.
Notice of Allowance issued counterpart U.S. Appl. No. 16/292,920 dated Nov. 10, 2021.
Notice of Allowance issued in counterpart U.S. Appl. No. 17/084,310 dated Nov. 12, 2021.
Notice of Allowance issued in counterpart U.S. Appl. No. 16/442,247 dated Nov. 15, 2021.
Final Office Action issued in counterpart U.S. Appl. No. 16/292,893 dated Nov. 15, 2021.
Luck, J. et al., Using standardized patients to measure physicians' practice: validation study using audio recordings. Bmj, 325(7366), 679 (2002).

* cited by examiner

SYSTEM AND METHOD FOR QUERYING DATA POINTS FROM GRAPH DATA STRUCTURES

TECHNICAL FIELD

This disclosure relates to data point querying systems and methods and, more particularly, to systems and methods for querying data points from graph data structures.

BACKGROUND

Doctors and/or healthcare providers must comply with a myriad of documentation requirements. Often, these documents are presented as forms where providers must click through. Users spend significant amounts of time interacting with confusing electronic form user interfaces that require a user to sequentially click through various screens to enter required information. Many conventional electronic forms include fields, buttons, selections, etc. that may or may not be relevant for a particular patient or data entry task. As such, many users of these electronic form user interfaces become confused and/or frustrated by the complexity associated with navigating electronic forms.

SUMMARY OF DISCLOSURE

In one implementation, a computer-implemented method is executed on a computing device and includes, but is not limited to, generating a graph data structure including a plurality of data points. A query for the graph data structure may be received via a user interface. At least one data point from the plurality of data points may be identified, via the user interface, in the graph data structure based upon, at least in part, the query. A selection of a data point from the identified at least one data point may be received via the user interface. The selected data point may be provided to one or more electronic data sources.

One or more of the following features may be included. Identifying the at least one data point from the plurality of data points in the graph data structure may include one or more of: rendering, via the user interface, the at least one data point in a list format and rendering, via the user interface, the at least one data point in a tree format. Identifying the at least one data point from the plurality of data points in the graph data structure may include determining one or more synonymous queries associated with the query and identifying, via the user interface, the at least one data point from the plurality of data points in the graph data structure based upon, at least in part, the one or more synonymous queries. Identifying the at least one data point from the plurality of data points in the graph data structure may include adding a data point to the graph data structure based upon, at least in part, the query. Each data point of the plurality of data points in the graph data structure may be associated with a unique identifier that maps to a standard classification code. Providing the selected data point to one or more data sources may include automatically populating at least a portion of at least one electronic form based upon, at least in part, the selected data point. The at least one electronic form may include at least one electronic health record form and the one or more electronic data sources may include one or more healthcare databases.

In another implementation, a computer program product resides on a non-transitory computer readable medium and has a plurality of instructions stored on it. When executed by a processor, the instructions cause the processor to perform operations including, but not limited to, generating a graph data structure including a plurality of data points. A query for the graph data structure may be received via a user interface. At least one data point from the plurality of data points may be identified, via the user interface, in the graph data structure based upon, at least in part, the query. A selection of a data point from the identified at least one data point may be received via the user interface. The selected data point may be provided to one or more electronic data sources.

One or more of the following features may be included. Identifying the at least one data point from the plurality of data points in the graph data structure may include one or more of: rendering, via the user interface, the at least one data point in a list format and rendering, via the user interface, the at least one data point in a tree format. Identifying the at least one data point from the plurality of data points in the graph data structure may include determining one or more synonymous queries associated with the query and identifying, via the user interface, the at least one data point from the plurality of data points in the graph data structure based upon, at least in part, the one or more synonymous queries. Identifying the at least one data point from the plurality of data points in the graph data structure may include adding a data point to the graph data structure based upon, at least in part, the query. Each data point of the plurality of data points in the graph data structure may be associated with a unique identifier that maps to a standard classification code. Providing the selected data point to one or more data sources may include automatically populating at least a portion of at least one electronic form based upon, at least in part, the selected data point. The at least one electronic form may include at least one electronic health record form and the one or more electronic data sources may include one or more healthcare databases.

In another implementation, a computing system includes a processor and memory is configured to perform operations including but not limited to, generating a graph data structure including a plurality of data points. A query for the graph data structure may be received via a user interface. At least one data point from the plurality of data points may be identified, via the user interface, in the graph data structure based upon, at least in part, the query. A selection of a data point from the identified at least one data point may be received via the user interface. The selected data point may be provided to one or more electronic data sources.

One or more of the following features may be included. Identifying the at least one data point from the plurality of data points in the graph data structure may include one or more of: rendering, via the user interface, the at least one data point in a list format and rendering, via the user interface, the at least one data point in a tree format. Identifying the at least one data point from the plurality of data points in the graph data structure may include determining one or more synonymous queries associated with the query and identifying, via the user interface, the at least one data point from the plurality of data points in the graph data structure based upon, at least in part, the one or more synonymous queries. Identifying the at least one data point from the plurality of data points in the graph data structure may include adding a data point to the graph data structure based upon, at least in part, the query. Each data point of the plurality of data points in the graph data structure may be associated with a unique identifier that maps to a standard classification code. Providing the selected data point to one or more data sources may include automatically populating at least a portion of at least one electronic form based upon, at least in part, the selected data point. The at least one electronic form may include at least one electronic health record form and the one or more electronic data sources may include one or more healthcare databases.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
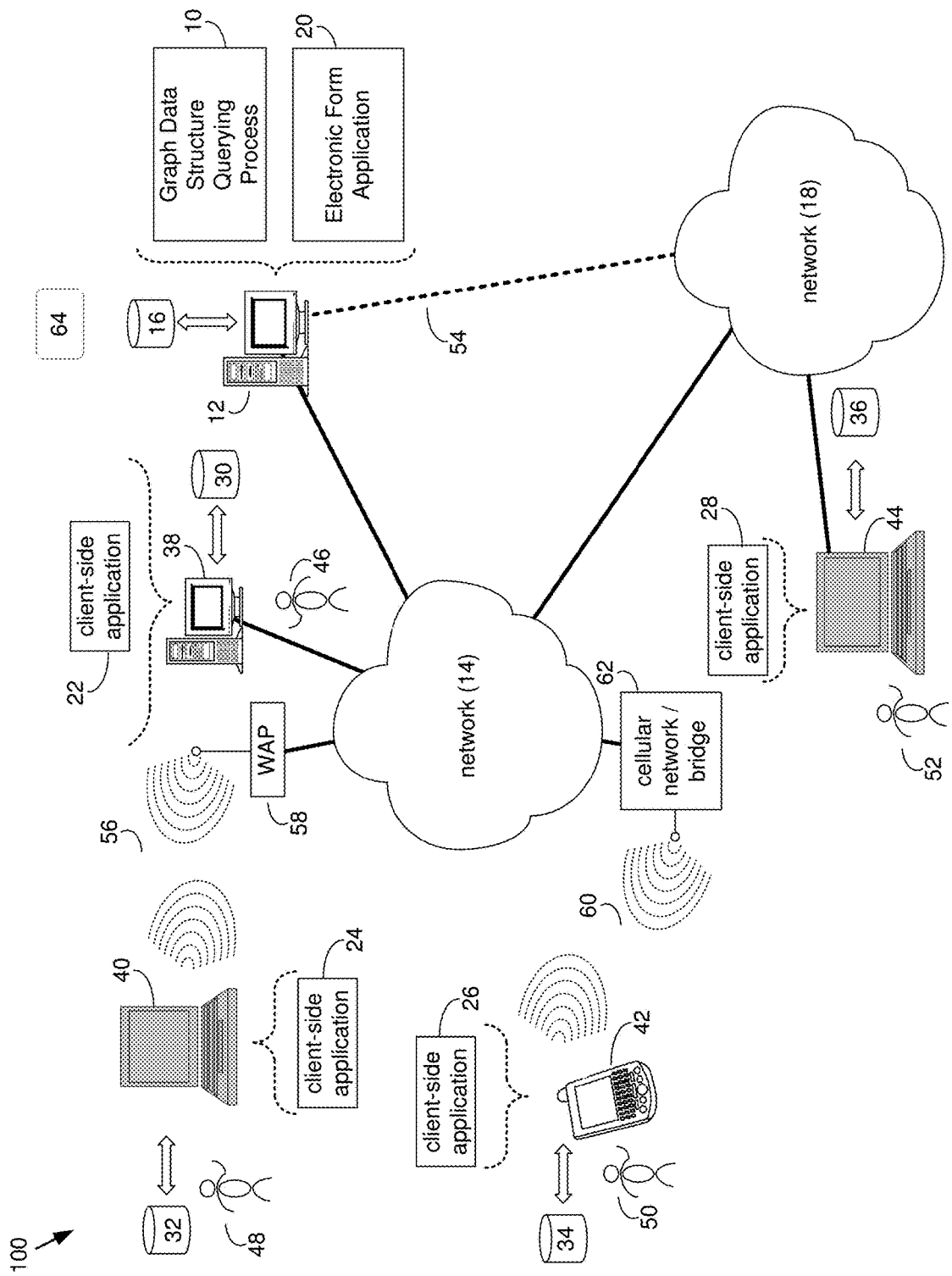
FIG. 1 is a diagrammatic view of an graph data structure querying process coupled to a distributed computing network.
Figure 2:
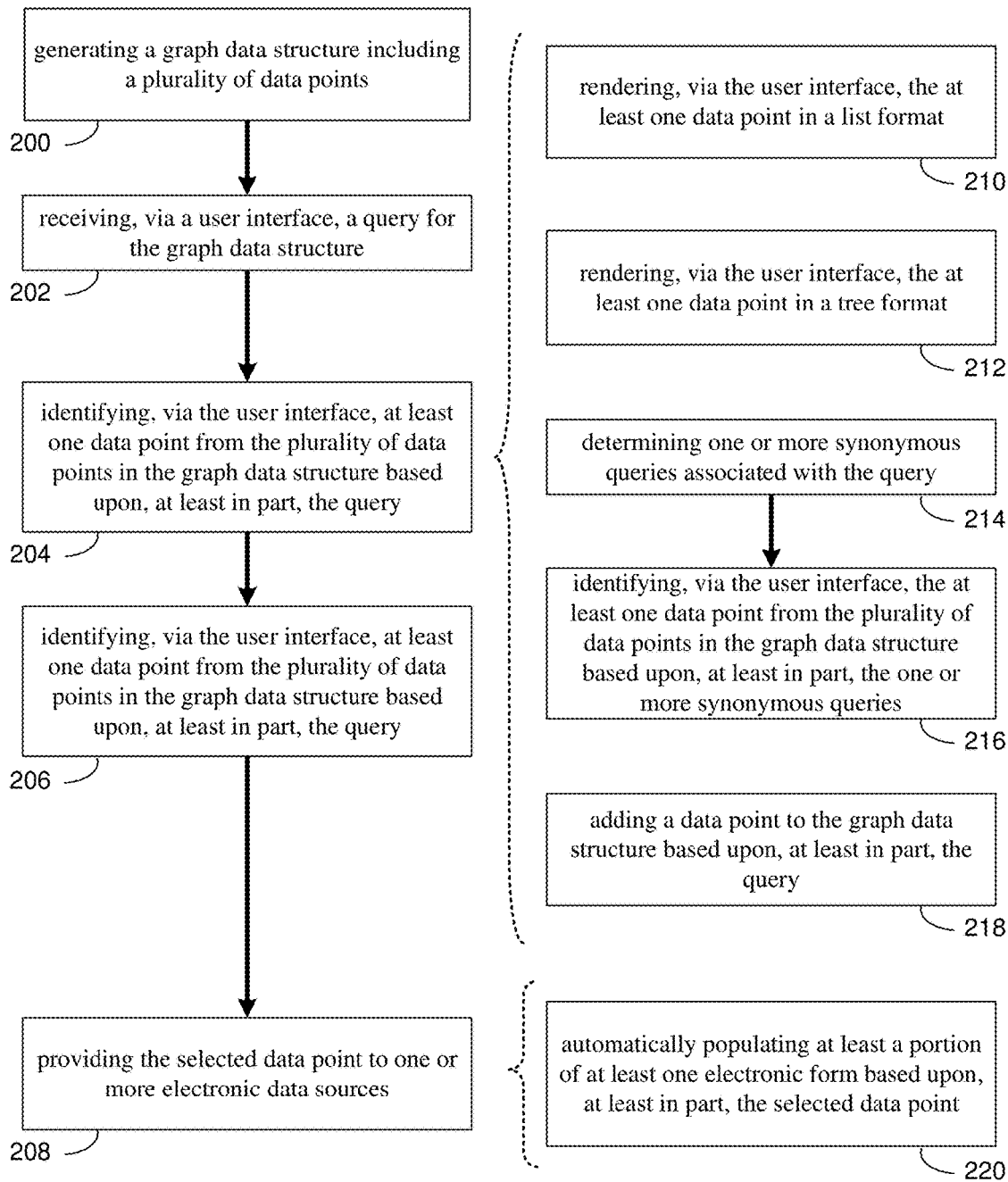
FIG. 2 is a flow chart of one implementation of the graph data structure querying process of FIG. 1.

Referring now to FIG. 1, there is shown graph data structure querying process 10 that may reside on and may be executed by a computing device 12, which may be connected to a network (e.g., network 14) (e.g., the internet or a local area network). Examples of computing device 12 (and/or one or more of the client electronic devices noted below) may include, but are not limited to, a personal computer(s), a laptop computer(s), mobile computing device(s), a server computer, a series of server computers, a mainframe computer(s), or a computing cloud(s). Computing device 12 may execute an operating system, for example, but not limited to, Microsoft® Windows®; Mac® OS X®; Red Hat® Linux®, or a custom operating system. (Microsoft and Windows are registered trademarks of Microsoft Corporation in the United States, other countries or both; Mac and OS X are registered trademarks of Apple Inc. in the United States, other countries or both; Red Hat is a registered trademark of Red Hat Corporation in the United States, other countries or both; and Linux is a registered trademark of Linus Torvalds in the United States, other countries or both).

As will be discussed below in greater detail, an graph data structure querying process, such as graph data structure querying process 10 of FIG. 1, may generate a graph data structure including a plurality of data points from one or more electronic forms. A query for the graph data structure may be received via a user interface. At least one data point from the plurality of data points may be identified, via the user interface, in the graph data structure based upon, at least in part, the query. A selection of a data point from the identified at least one data point may be received via the user interface. The selected data point may be provided to one or more electronic data sources.

The instruction sets and subroutines of graph data structure querying process 10, which may be stored on storage device 16 coupled to computing device 12, may be executed by one or more processors (not shown) and one or more memory architectures (not shown) included within computing device 12. Storage device 16 may include but is not limited to: a hard disk drive; a flash drive, a tape drive; an optical drive; a RAID array; a random access memory (RAM); and a read-only memory (ROM).

Network 14 may be connected to one or more secondary networks (e.g., network 18), examples of which may include but are not limited to: a local area network; a wide area network; or an intranet, for example.

Graph data structure querying process 10 may be a stand-alone application that interfaces with an applet/application that is accessed via client applications 22, 24, 26, 28, 66. In some embodiments, graph data structure querying process 10 may be, in whole or in part, distributed in a cloud computing topology. In this way, computing device 12 and storage device 16 may refer to multiple devices, which may also be distributed throughout network 14 and/or network 18.

Computing device 12 may execute an electronic form application (e.g., electronic form application 20), examples of which may include, but are not limited to, user interfaces that facilitate the entry of data into a structured data list, such as an electronic form. In examples involving the healthcare industry, electronic form application 20 may generally include ambient clinical intelligence systems, clinical information systems, electronic health record (EHR) systems provided by various EHR vendors (e.g., Epic, Allscripts, CureMD, etc.), etc. However, it will be appreciated that other non-healthcare related electronic form applications may be used within the scope of the present disclosure. Graph data structure querying process 10 and/or electronic form application 20 may be accessed via client applications 22, 24, 26, 28, 68. Graph data structure querying process 10 may be a stand-alone application, or may be an applet/application/script/extension that may interact with and/or be executed within electronic form application 20, a component of electronic form application 20, and/or one or more of client applications 22, 24, 26, 28, 68. Electronic form application 20 may be a stand-alone application, or may be an applet/application/script/extension that may interact with and/or be executed within graph data structure querying process 10, a component of graph data structure querying process 10, and/or one or more of client applications 22, 24, 26, 28, 68. One or more of client applications 22, 24, 26, 28, 68 may be a stand-alone application, or may be an applet/application/script/extension that may interact with and/or be executed within and/or be a component of graph data structure querying process 10 and/or electronic form application 20. Examples of client applications 22, 24, 26, 28, 68 may include, but are not limited to, applications that receive queries to search for content from one or more databases, servers, cloud storage servers, etc., a textual and/or a graphical user interface, a customized web browser, a plugin, an Application Programming Interface (API), or a custom application. The instruction sets and subroutines of client applications 22, 24, 26, 28, 68 which may be stored on storage devices 30, 32, 34, 36, coupled to client electronic devices 38, 40, 42, 44 may be executed by one or more processors (not shown) and one or more memory architectures (not shown) incorporated into client electronic devices 38, 40, 42, 44.

Storage devices 30, 32, 34, 36, may include but are not limited to: hard disk drives; flash drives, tape drives; optical drives; RAID arrays; random access memories (RAM); and read-only memories (ROM). Examples of client electronic devices 38, 40, 42, 44 (and/or computing device 12) may include, but are not limited to, a personal computer (e.g., client electronic device 38), a laptop computer (e.g., client electronic device 40), a smart/data-enabled, cellular phone (e.g., client electronic device 42), a notebook computer (e.g., client electronic device 44), a tablet (not shown), a server (not shown), a television (not shown), a smart television (not shown), a media (e.g., video, photo, etc.) capturing device (not shown), and a dedicated network device (not shown). Client electronic devices 38, 40, 42, 44 may each execute an operating system, examples of which may include but are not limited to, Microsoft® Windows®; Mac® OS X®; Red Hat® Linux®, Windows® Mobile, Chrome OS, Blackberry OS, Fire OS, or a custom operating system.

One or more of client applications 22, 24, 26, 28 may be configured to effectuate some or all of the functionality of graph data structure querying process 10 (and vice versa). Accordingly, graph data structure querying process 10 may be a purely server-side application, a purely client-side application, or a hybrid server-side/client-side application that is cooperatively executed by one or more of client applications 22, 24, 26, 28, 68 and/or graph data structure querying process 10.

One or more of client applications 22, 24, 26, 28 may be configured to effectuate some or all of the functionality of electronic form application 20 (and vice versa). Accordingly, electronic form application 20 may be a purely server-side application, a purely client-side application, or a hybrid server-side/client-side application that is cooperatively executed by one or more of client applications 22, 24, 26, 28 and/or electronic form application 20. As one or more of client applications 22, 24, 26, 28 graph data structure querying process 10, and electronic form application 20, taken singly or in any combination, may effectuate some or all of the same functionality, any description of effectuating such functionality via one or more of client applications 22, 24, 26, 28 graph data structure querying process 10, electronic form application 20, or combination thereof, and any described interaction(s) between one or more of client applications 22, 24, 26, 28 graph data structure querying process 10, electronic form application 20, or combination thereof to effectuate such functionality, should be taken as an example only and not to limit the scope of the disclosure.

Users 46, 48, 50, 52 may access computing device 12 and graph data structure querying process 10 (e.g., using one or more of client electronic devices 38, 40, 42, 44) directly or indirectly through network 14 or through secondary network 18. Further, computing device 12 may be connected to network 14 through secondary network 18, as illustrated with phantom link line 54. Graph data structure querying process 10 may include one or more user interfaces, such as browsers and textual or graphical user interfaces, through which users 46, 48, 50, 52 may access graph data structure querying process 10.

The various client electronic devices may be directly or indirectly coupled to network 14 (or network 18). For example, client electronic device 38 is shown directly coupled to network 14 via a hardwired network connection. Further, client electronic device 44 is shown directly coupled to network 18 via a hardwired network connection. Client electronic device 40 is shown wirelessly coupled to network 14 via wireless communication channel 56 established between client electronic device 40 and wireless access point (i.e., WAP) 58, which is shown directly coupled to network 14. WAP 58 may be, for example, an IEEE 800.11a, 800.11b, 800.11g, Wi-Fi®, and/or Bluetooth™ (including Bluetooth™ Low Energy) device that is capable of establishing wireless communication channel 56 between client electronic device 40 and WAP 58. Client electronic device 42 is shown wirelessly coupled to network 14 via wireless communication channel 60 established between client electronic device 42 and cellular network/bridge 62, which is shown directly coupled to network 14.

Some or all of the IEEE 800.11x specifications may use Ethernet protocol and carrier sense multiple access with collision avoidance (i.e., CSMA/CA) for path sharing. The various 800.11x specifications may use phase-shift keying (i.e., PSK) modulation or complementary code keying (i.e., CCK) modulation, for example. Bluetooth™ (including Bluetooth™ Low Energy) is a telecommunications industry specification that allows, e.g., mobile phones, computers, smart phones, and other electronic devices to be interconnected using a short-range wireless connection. Other forms of interconnection (e.g., Near Field Communication (NFC)) may also be used.

As discussed above and referring also at least to FIGS. 2-11, graph data structure querying process 10 may generate 200 a graph data structure including a plurality of data points from one or more electronic forms. A query for the graph data structure may be received 202 via a user interface. At least one data point from the plurality of data points may be identified 204, via the user interface, in the graph data structure based upon, at least in part, the query. A selection of a data point from the identified at least one data point may be received 206 via the user interface. The selected data point may be provided 208 to one or more electronic data sources.

In some implementations consistent with the present disclosure, systems and methods may be provided for populating electronic forms or other structured data lists using graph data structures. As discussed above, doctors and/or healthcare providers must comply with a myriad of documentation requirements. Often, these documents are presented as forms users must click through. Users may spend significant amounts of time interacting with confusing electronic form user interfaces that require a user to sequentially click through various screens to enter required information. Many conventional electronic forms include fields, buttons, selections, etc. that may not be relevant for a particular data entry task. As such, many users of these electronic form user interfaces become confused and/or frustrated by the complexity associated with navigating electronic forms.

As will be discussed in greater detail below, embodiments of the present disclosure may allow users to save time when interacting with a user interface by generating a graph data structure (e.g., from one or more structured data lists or electronic forms) and providing a user interface for querying data points from the graph data structure. In this manner, embodiments of the present disclosure may allow a user to access any portion of an electronic form from a query. In this manner, the complexity and amount of time required to populate or fill electronic forms may be reduced through the interaction of a query and the graph data structure.

Figure 3:
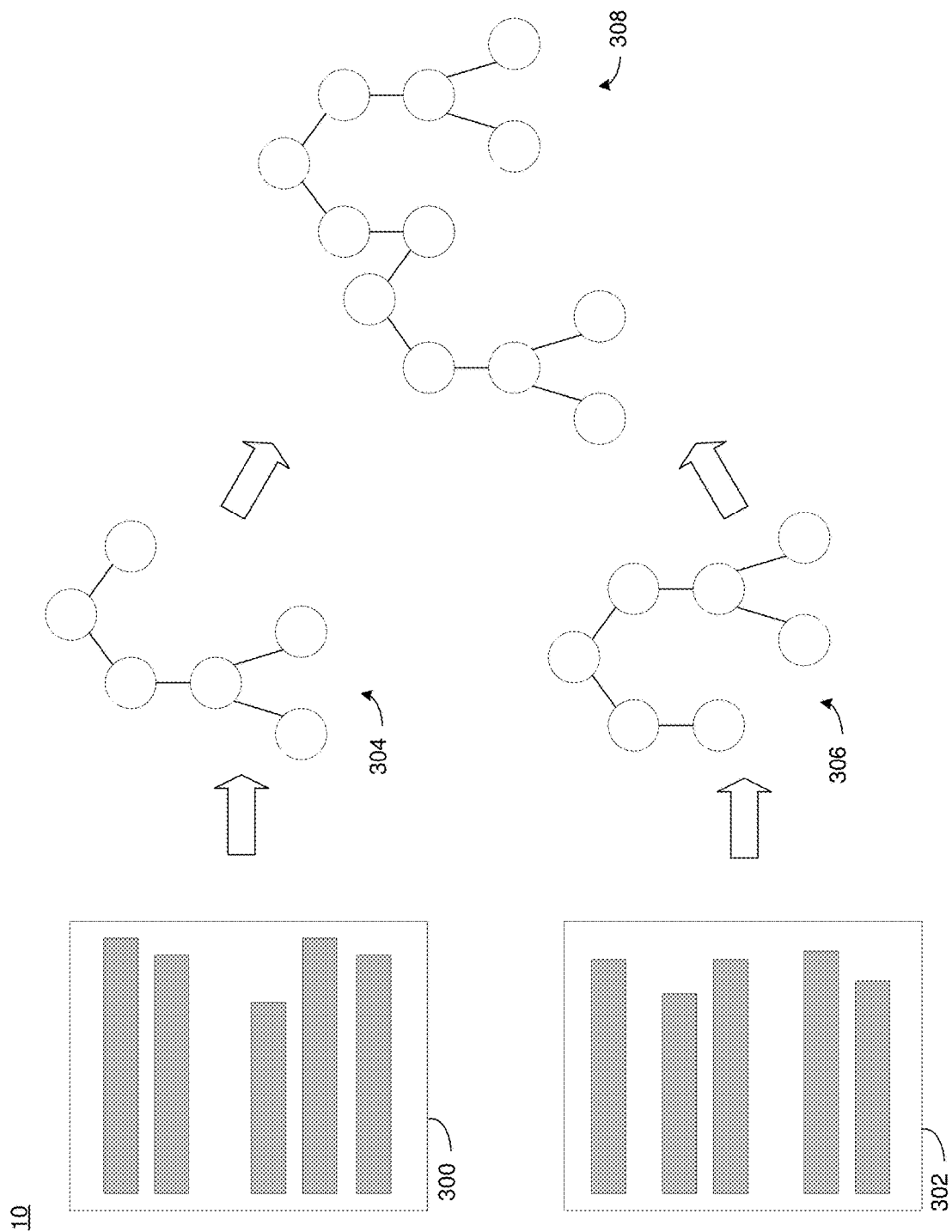
FIG. 3 is a diagrammatic view of a plurality of electronic forms and a graph data structure generated by one implementation of the graph data structure querying process of FIG. 1.

Referring also to FIG. 3 and in some implementations, graph data structure querying process 10 may generate 200 a graph data structure including a plurality of data points.

For example, graph data structure querying process 10 may generate 200 a graph data structure including a plurality of data points from any structured data list (e.g., an electronic form, a table, a document, and/or any structured data list (e.g., loosely structured, rigidly structured, etc.)). In some implementations, the plurality of data points can be (but do not have to be) extracted from an electronic form, or other structured user interface. In some implementations, graph data structure querying process 10 may receive one or more electronic forms (e.g., forms 300, 302). An electronic form may generally include a form with one or more data fields, buttons, selections, menus, etc. accessible via a user interface (e.g., electronic form application 20). In one example, the one or more electronic forms may include one or more electronic health records (EHRs). As known in the art, an EHR is an electronically-stored health record associated with a patient. In some implementations, EHRs may be accessible (e.g., created, modified, read, etc.) by various electronic health applications. In some implementations and as will be discussed in greater detail below, EHRs may be stored in one or more healthcare databases. While an example has been provided of an EHR as an electronic form, it will be appreciated that any type of electronic form may be used within the scope of the present disclosure. Additionally, while an electronic form has been provided as an example of a structured data list, it will be appreciated that any structured data list may be used within the scope of the present disclosure.

Referring again to FIG. 3 and in some implementations, graph data structure querying process 10 may generate 200 a graph data structure from one or more electronic forms. A graph data structure may generally include a mathematical structure demonstrating a relationship between a set of objects (e.g., nodes or points) where some pairs of objects are connected by links. Interconnected objects may be represented by points termed as vertices, and the links that connect the vertices may be referred to as edges. In some implementations, a graph data structure need not be contiguous. In this manner, a graph data structure may include multiple, disconnected graph clusters of varying depth and complexity. In some implementations, graph data structure querying process 10 may generate 200 a directed acyclic graph (DAG) to represent the one or more data points of the one or more forms. A directed acyclic graph may generally include a directed graph with nodes and edges, with each edge directed from one node to another, such that there is no way to start at any one node and follow a consistently-directed sequence of edges that eventually loops back to that node again. Equivalently, a DAG may be a directed graph that has a topological ordering (e.g., a sequence of the nodes such that every edge is directed from earlier to later in the sequence). However, it will be appreciated that any graph data structure may be used within the scope of the present disclosure.

As discussed above, each electronic form (e.g., forms 300, 302) may include various portions (e.g., data fields, menus, buttons, selections, etc.). Each portion of the electronic form may be associated with one or more particular values. For example, form 300 may include data fields for entering the results of e.g., a physical examination. Different fields of electronic form 300 may allow a user to input the results of e.g., a musculoskeletal examination. In some implementations, each data field of form 300 may have expected or permitted values for various elements of e.g., a musculoskeletal examination. For example, a user may be able to select a subset of a musculoskeletal examination (e.g., an elbow examination, a shoulder examination, a knee examination, an ankle examination, etc.) in form 300 and may populate data fields pertaining to that examination. Additional data fields may be included in form 300 for providing a desired level of data granularity associated with the form.

As shown in FIG. 3 and in some implementations, graph data structure querying process 10 may generate 200 graph data structure 304 using form 300 and graph data structure 306 using form 302. For example, the circles (e.g., nodes) of graph data structure 304 may represent particular data points from form 300 and the nodes of graph data structure 306 may represent particular data points from form 302. In some embodiments, graph data structures may be generated 200 from one or more graph data structures. For example and as shown in FIG. 3, graph data structure 308 may be generated by merging graph data structures 304, 306. In this manner, graph data structure querying process 10 may generate a graph data structure including several thousand data points consolidated into a single structure. It will be appreciated that any number of electronic forms may be used to generate any number of graph data structures within the scope of the present disclosure. For example, a plurality of electronic forms may be processed by graph data structure querying process 10 (e.g., extracting data fields, buttons, selectable features, etc.) to generate a plurality of graph data structures which may be merged into a single graph data structure.

Figure 4:
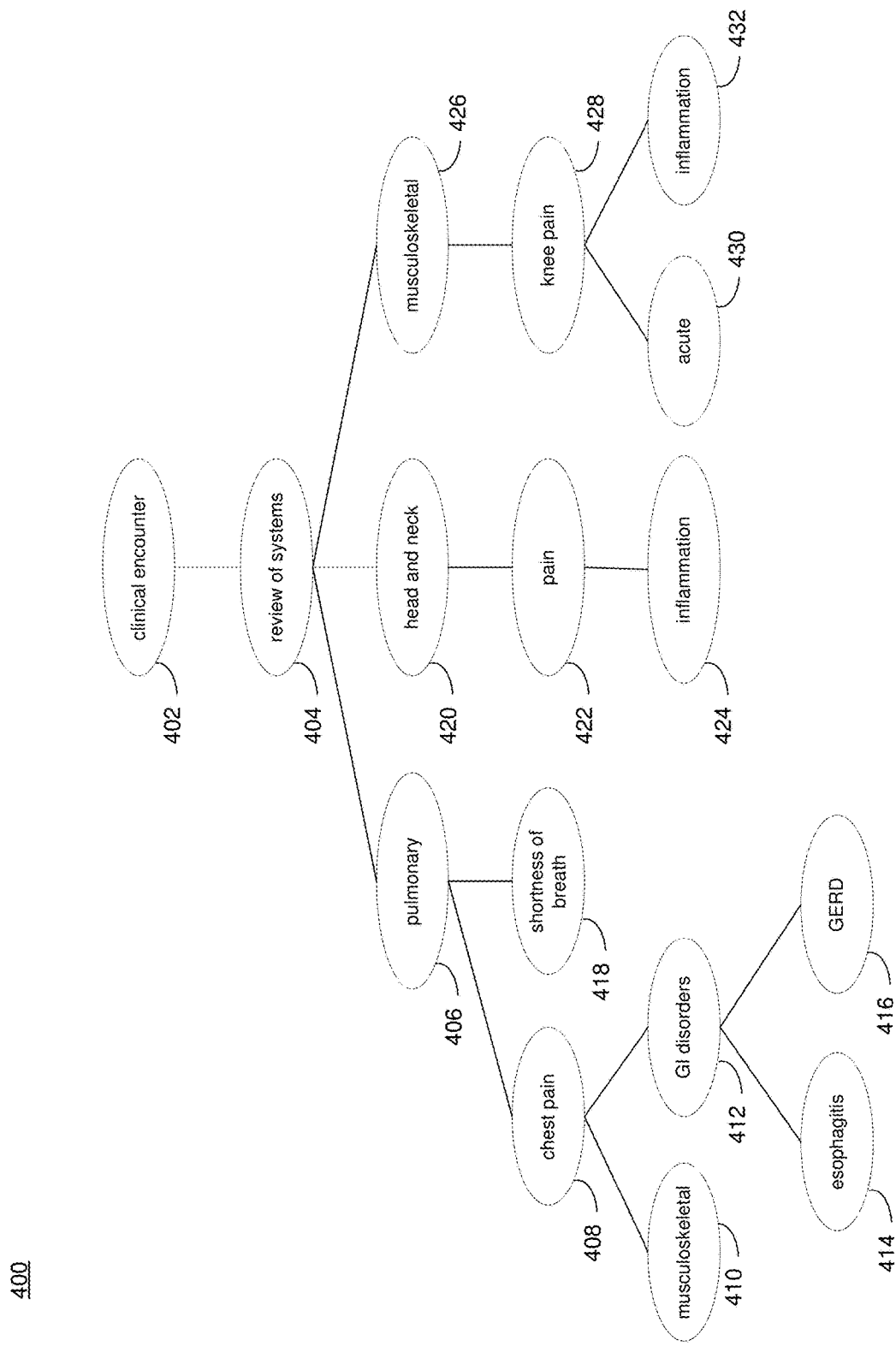
FIG. 4 is an exemplary graph data structure according to one implementation of the graph data structure querying process of FIG. 1.

Referring also to FIG. 4 and in some implementations, graph data structure querying process 10 may generate 200 a graph data structure (e.g., graph data structure 400) with one or more data points (e.g., data points 402, 402, 406, 408, 410, 412, 414, 416, 418, 420, 422, 424, 426, 428, 430, 432). In this example, nodes or data points of graph data structure 400 may be representative of data portions of a structured data list. For example, the nodes of graph data structure 400 may be representative of various data fields, buttons, selections, etc. from one or more electronic forms. While the example graph data structure of FIG. 4 includes an example of a clinical encounter and data points associated with a clinical encounter, it will be appreciated that graph data structure querying process 10 may generate 200 a graph data structure with data points associated with other types of information or data. In some embodiments, sequentially entered information from the perspective of a structured data list (e.g., an electronic form) may be represented in a graph data structure as directed edges between nodes. For example, selection of a "clinical encounter" option in an structured data list (e.g., an electronic form) may lead to an option for selection of one or more options or types of clinical encounters (e.g., review of systems). Graph data structure querying process 10 may generate 200 a data point for the "clinical encounter" option of structured data list (e.g., data point 402), a data point for the "review of systems" option of the structured data list (e.g., data point 404), and a link or edge between these data points. Selection of a "review of systems" option may provide options for selection of e.g., a "pulmonary"; "head and neck"; and "musculoskeletal". As each element of the structured data list (e.g., form) is processed, graph data structure querying process 10 may generate 200 edges between nodes or data points in the graph data structure.

In some implementations, graph data structure querying process 10 may receive 202 via a user interface, a query for the graph data structure. Referring also to the example of FIGS. 5-9 and in some implementations, graph data structure querying process 10 may provide or render a user interface (e.g., user interface 500) with a query bar or search bar (e.g., query bar 502) configured to receive a query (e.g., query 64) for searching or querying a graph data structure. In some implementations, user interface 500 may be web accessible (e.g., accessible by utilizing a browser), may be a portion of an electronic form application (e.g., electronic form application 20), and/or may be a stand-alone application. As will be discussed in greater detail below and in some implementations, a graph data structure may be exposed to the user in a very simple (e.g., "flat") user interface (e.g., user interface 500) by hiding the complexity of the underlying, multi-layered and jargon-heavy graph data structure. In this manner, where conventional user interfaces require a user to access a certain number of data fields of an electronic form and/or access a specific sequence of data fields or other portions of an electronic form, embodiments of the present disclosure may allow a user to simply provide a query that may be received by graph data structure querying process 10 for querying the graph data structure without being restricted by the complexities and flow issues of an electronic form. In this manner, the user experience and efficiency in interacting with electronic forms (e.g., user interfaces providing electronic forms) may be improved.

Figure 5:
FIGS. 5-9 are diagrammatic views of querying a graph data structure, via a user interface, according to various implementations of the graph data structure querying process of FIG. 1.

In some implementations, graph data structure querying process 10 may identify 204, via the user interface, at least one data point from the plurality of data points in the graph data structure based upon, at least in part, the query. In the example of FIG. 5 and in some implementations, suppose a user inputs (e.g., via a keyboard, voice command, touch screen, etc.) a query into query bar 502 of user interface 500. In some implementations, graph data structure querying process 10 may evaluate (e.g., with each keystroke) each substring, word, and/or phrase to match at least a portion of the query with a data point in the underlying graph data structure. In this example, suppose a user is interested in adding e.g., an observation from a physical examination to an electronic form. Specifically, assume that the user would like to add "inflammation knee pain bursitis" to an electronic data source (e.g., an electronic form). As discussed above, conventional approaches with current user interfaces may make this task difficult by requiring the user to click through many successive pages and options to enter content. While this example is specific to a clinical encounter and an EHR, it will be appreciated that any type of data may be received by graph data structure querying process 10 for providing data points to an electronic source based on a query of a graph data structure. As the user enters the sequence of letters "i" and "n", graph data structure querying process 10 may identify 204 at least one data point from the plurality of data points in the graph data structure based upon, at least in part, the query (e.g., "in"). For example and as shown in FIG. 5, in response to receiving "in", graph data structure querying process 10 may query the graph data structure to identify 204 at least one data point in the user interface (e.g., at least one data point 504). As shown in FIG. 5, at least one data point 504 identified 204 by graph data structure querying process 10 may include a plurality of data points. In some implementations, graph data structure querying process 10 may identify 204 the at least one data point from the plurality of data points by identifying 204 at least a portion of the query in a "leaf" or terminal node of the graph data structure.

In some implementations, identifying 204 the at least one data point from the plurality of data points in the graph data structure includes one or more of: rendering 210, via the user interface, the at least one data point in a list format and rendering 212, via the user interface, the at least one data point in a tree format. For example and as shown in FIGS. 5-9, the at least one data point (e.g., at least one data point 504) identified 204 by graph data structure querying process 10 may be displayed or rendered 210 in user interface 500 as a list format (e.g., "clinical encounter"→"review of systems"→"head and neck"→"pain"→"inflammation"). Referring again to FIG. 4 and in some implementations, the list format of the at least one data point identified 204 by graph data structure querying process 10 may include a listing of each node in a graph data structure from a "root" node (e.g., "clinical encounter") to a "leaf" node (e.g., "inflammation") of a graph data structure.

In some implementations, graph data structure querying process 10 may render the at least one data point in a tree format. For example and as shown in FIG. 4, the graph data structure may be represented graphically with shapes representative of nodes and lines between nodes representative of relationships between the nodes. In this manner, graph data structure querying process 10 may display portions of the graph data structure in a tree format when rendering the at least one data point identified 204 from the graph data structure. While a list format and a tree format have been described as examples of how the at least one data point may be presented to a user in a user interface, it will be appreciated that other formats are possible within the scope of the present disclosure.

Figure 6:
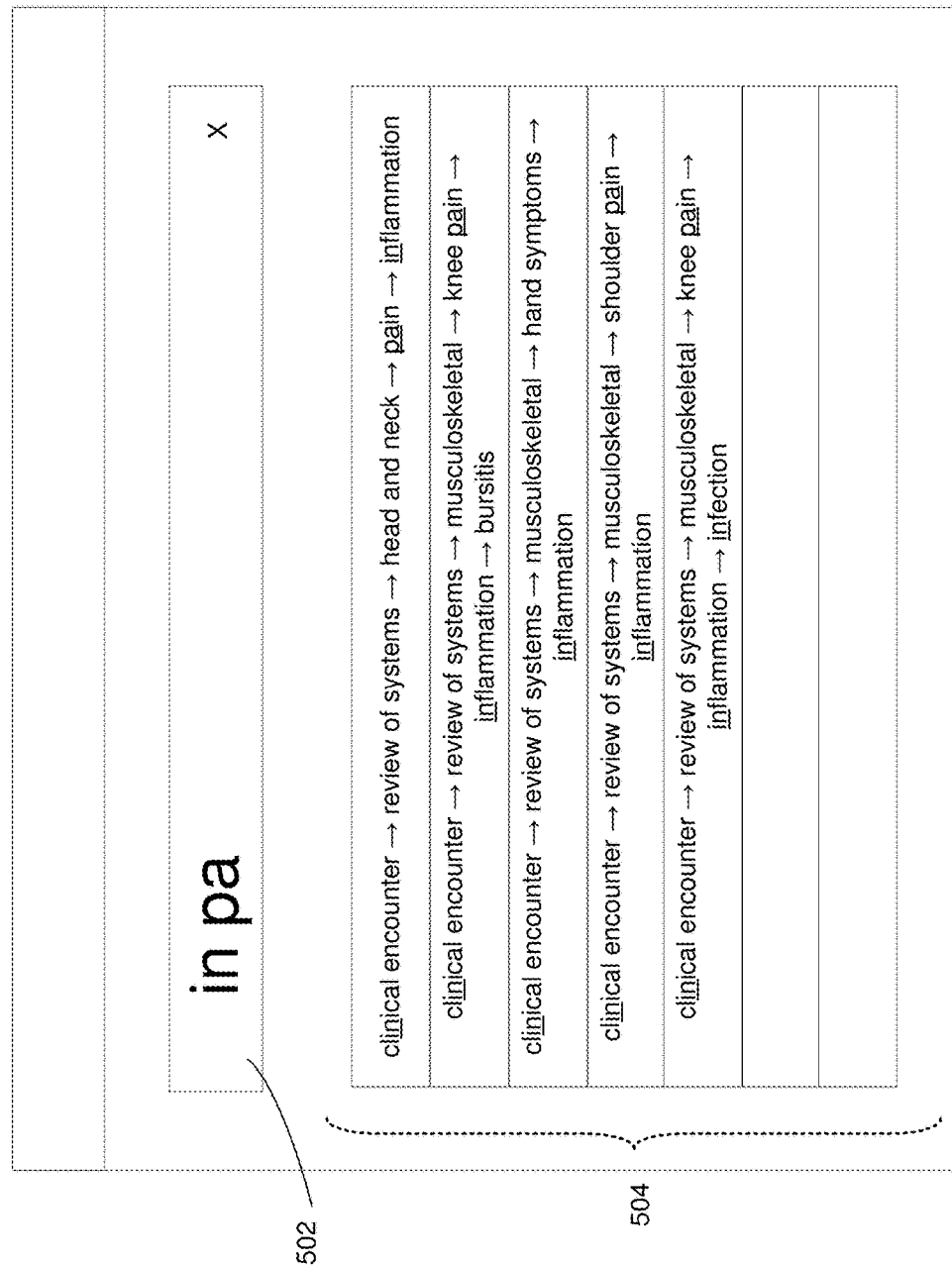

Referring also to FIG. 6 and in some implementations, graph data structure querying process 10 may narrow down or filter out portions of the plurality of data points to at least one data point (e.g., at least one data point 504) identified 204 in response to the query. In some implementations, graph data structure querying process 10 may identify 204 the at least one data point (e.g., at least one data point 504) in a ranking of data points. For example and in some implementations, graph data structure querying process 10 may rank the at least one data point e.g., from most relevant to least relevant. In some implementations, relevance may be configured or algorithmically learned (e.g., implementations of the present disclosure using machine-learning systems) based upon, at least in part, one or more relevance factors. Relevance factors may generally include factors that influence how relevant as data point is to a query. For example, a "most frequently used" relevance factor may rank more frequently used data points higher in the display of data points. In another example, a "least distance clinically" relevance factor may be a healthcare specific relevance factor that may rank data points higher that are clinically relevant based on one or more clinical rules (e.g., commonly associated or relevant symptoms or observations) and/or based on proximity within the graph data structure (e.g., proximate nodes). In yet another example, a "least distance phonetically" relevance factor may rank data points higher that are more relevant based on phonetical similar or proximity. While examples of various relevance factors have been provided, it will be appreciated that any relevance factor may be used within the scope of the present disclosure to rank data points.

In some implementations, graph data structure querying process 10 may identify at least one data point based upon, at least in part, at least a portion of the query. For example, suppose a user inputs or provides "in" into the query bar (e.g., query bar 502) as shown in FIG. 5. Suppose that instead of providing the remainder of the word "inflammation", the user inputs a space character and the letters "pa". Conventional search algorithms may include a rule that the string "in" is a complete word once a space character is detected. In some implementations, graph data structure querying process 10 may identify the sub-string "in" and the newly entered "pa" in the graph data structure. For example and as shown in FIG. 6, graph data structure querying process 10 may identify 204 a data point with "head and neck"→"pain"→"inflammation" based upon the query "in pa". However, it will also be appreciated that implementations of the present disclosure may also include rules that determine that a string is a complete word once a space character is detected.

In some implementations, identifying 204 the at least one data point from the plurality of data points in the graph data structure may include determining 214 one or more synonymous queries associated with the query. In some implementations, graph data structure querying process 10 may determine 214 one or more synonyms and/or colloquialisms associated with at least a portion of the query. For example and continuing with the above example where a user inputs (e.g., via a keyboard, touch screen, voice command, etc.) "in pa" into the query bar, graph data structure querying process 10 may identify at least one data point associated with "pain" based upon, at least in part, at least a portion of the query (e.g., "pa"). In some implementations, graph data structure querying process 10 may determine 214 one or more synonymous queries associated with the query. In this example, graph data structure querying process 10 may determine a synonymous query (e.g., "hurt") associated with the query (e.g., "pain" from "pa" of the query). In some implementations, graph data structure querying process 10 may access one or more databases for determining 214 one or more synonymous queries. In some implementations, graph data structure querying process 10 may learn (e.g., via a machine-learning system) from user selections to determine 214 synonymous queries associated with a query. While an example of a single synonymous query has been provided, it will be appreciated that any number of synonymous queries may be determined 214 within the scope of the present disclosure.

In some implementations, graph data structure querying process 10 may identify 216, via the user interface, the at least one data point from the plurality of data points in the graph data structure based upon, at least in part, the one or more synonymous queries. Returning to the above example of a query (e.g., "in pa"), graph data structure querying process 10 may identify 216 at least one data point in the graph data structure associated with the word "hurt" as a synonymous query for the word "pain" based on the query "pa". In this manner, embodiments of the present disclosure may provide a more flexible approach to entering data into an electronic form. For example, instead of only searching the exact phrase of a query, graph data structure querying process 10 may provide at least one data point based upon, at least in part, one or more synonymous queries.

Figure 7:
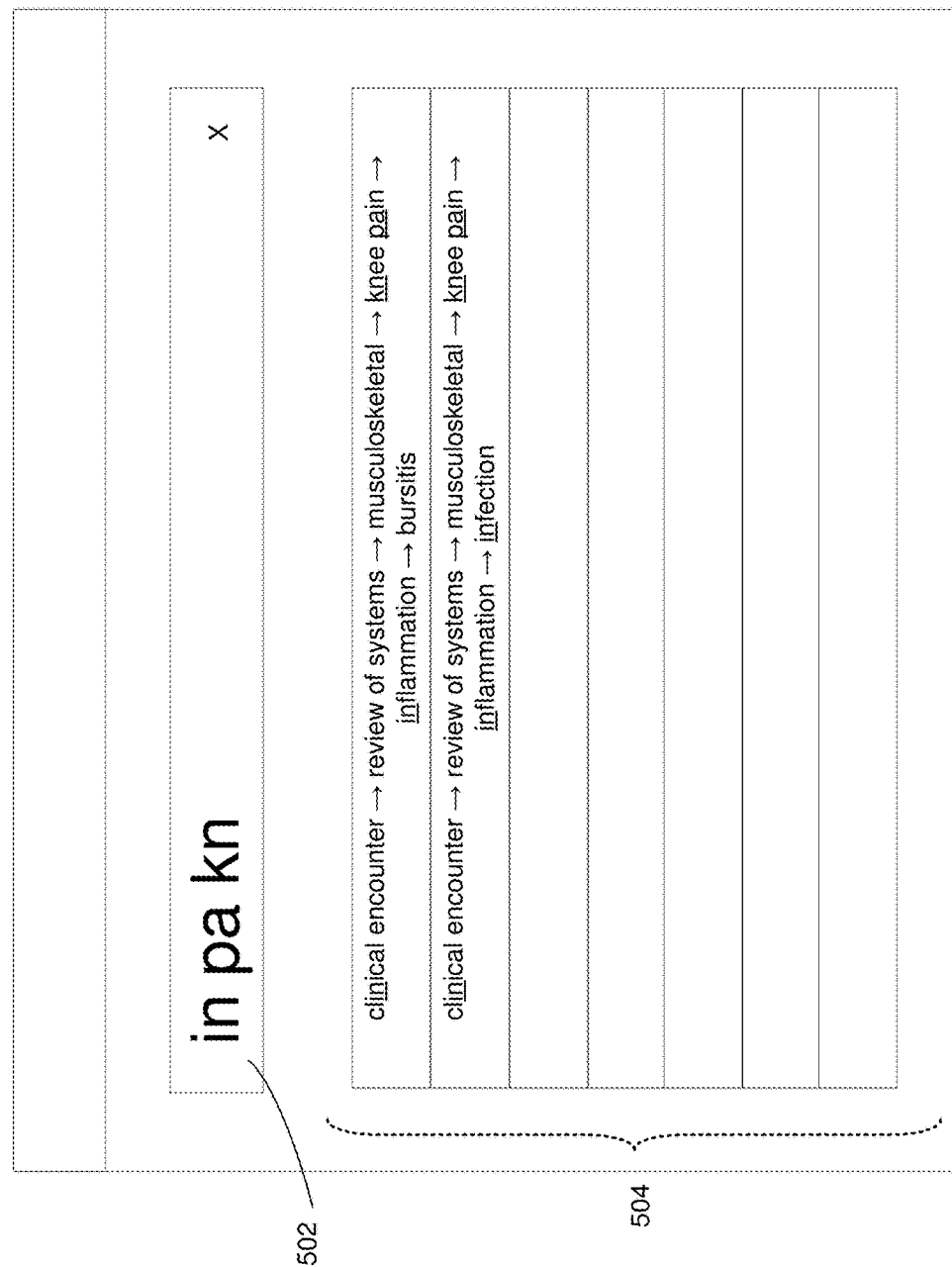

Referring also to FIG. 7 and in some implementations, graph data structure querying process 10 may identify 204 the at least one data point independent of the order of the portions of the query. For example and as shown in FIG. 7, suppose a user adds another space character and the letters "kn". In some conventional search algorithms, a rule may provide results with sub-strings in an identical order as received in the search bar. In some implementations, graph data structure querying process 10 may identify the portions of the query (e.g., "in", "pa", and "kn") in any order or combination. For example and as shown in FIG. 7, graph data structure querying process 10 may identify 204 the data point "knee pain"→"inflammation"→"bursitis" based upon, at least in part, the query (e.g., "in pa kn"). However, it will also be appreciated that implementations of the present disclosure may also include rules that identify the portions of the query in a specific order (e.g., the order received in the query bar).

Figure 8:
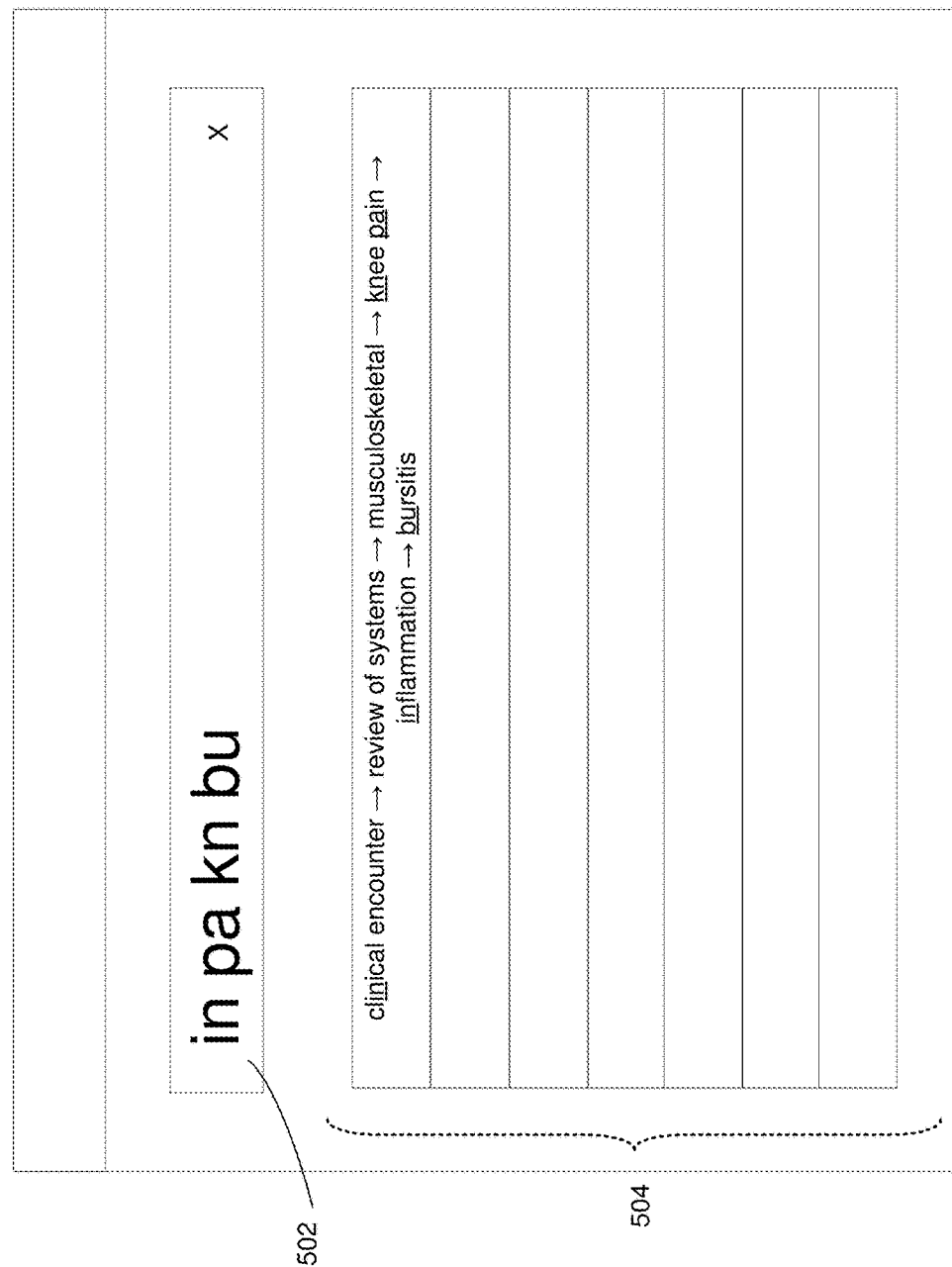

Referring also to the example of FIG. 8 and in some implementations, suppose a user adds another space character and adds the letters "bu" to the query shown in query bar 502. In response to this addition, graph data structure querying process 10 may identify a single data portion (e.g., data portion 504) representative of e.g., bursitis of a knee observed during a review of the knee as part of a clinical encounter.

In some implementations, identifying 204 the at least one data point from the plurality of data points in the graph data structure may include adding 218 a data point to the graph data structure based upon, at least in part, the query. In some implementations, graph data structure querying process 10 may provide a user with the ability to modify one or more data points of the graph data structure. For example and in some implementations, graph data structure querying process 10 may provide one or more tools, buttons, features, etc. in the user interface for adding, removing, hiding, duplicating, de-duplicating, etc. data points in the graph data structure.

In some implementations, graph data structure querying process 10 may provide a user with the ability to add and/or remove nodes of the graph data structure. For example, suppose a user believes that graph data structure querying process 10 generates a data point that fails to accurately represent or include a particular feature (e.g., a new medication is not included, an outdated reference to a certain medical procedure appears in a list of data points identified by graph data structure querying process 10, etc.). In this example, a user may provide a command (e.g., a button, voice-command, etc.) in a user interface to add and/or edit a data point within the graph data structure. In another example, suppose a user believes that graph data structure querying process 10 generates a data point that includes duplicates of a particular portion of an electronic form. In this example, a user may provide a command (e.g., a button, voice-command, etc.) in a user interface to remove a node of the graph data structure. In some implementations, adding 218 a data point (e.g., a new data point) to the graph data structure may be available to all users while removing a data point may be limited to certain users (e.g., administrators of graph data structure querying process 10). It will be appreciated that the ability to perform various functions on the graph data structure may be dependent upon a role of a user. In some implementations, adding 218 a data point may be provided in the user interface in response to graph data structure querying process 10 not being able to identify 204 at least one data point for the query. In this manner, a user may update the graph data structure with at least one data point for future queries. In some implementations, graph data structure querying process 10 may make the newly added data point available to other users querying the graph data structure.

Figure 9:
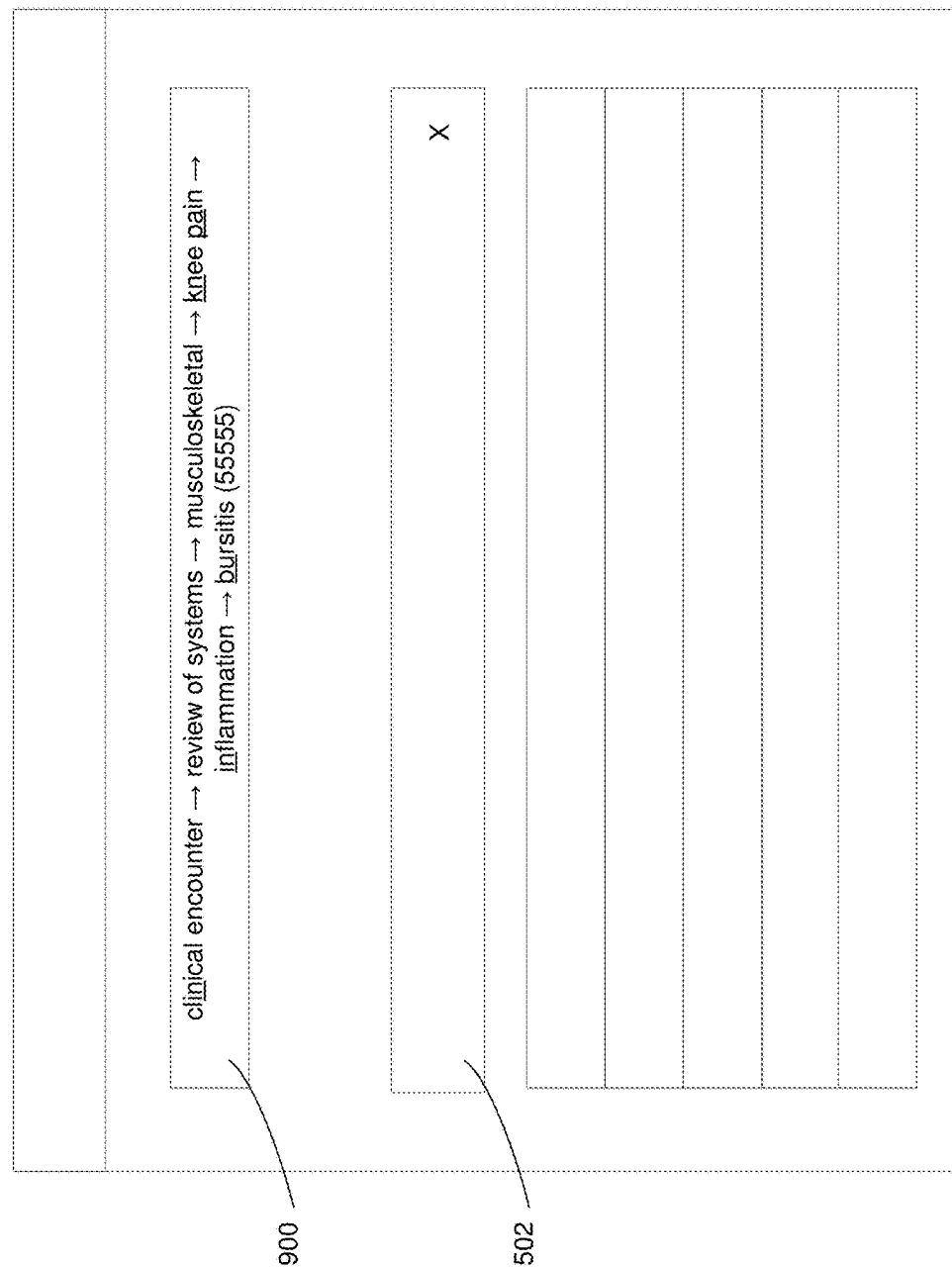

In some implementations, graph data structure querying process 10 may receive 206, via the user interface, a selection of a data point from the identified at least one data point. Referring also to FIGS. 8-9 and in some implementations, a user may select a data point from the at least one data point (e.g., at least one data point 504). In some implementations and as shown in FIG. 9, graph data structure querying process 10 may include the selected data point (e.g., selected data point 900) in a separate portion of the user interface (e.g., user interface 500). As will be discussed in greater detail below and in some implementations, the selected data point may be combined with other data points for populating one or more electronic forms and/or for storage in one or more electronic data sources.

In some implementations, each data point of the plurality of data points in the graph data structure may be associated with a unique identifier that maps to a standard classification code. For example and in some implementations, graph data structure querying process 10 may associate each data point of the plurality of data points of the graph data structure with a unique identifier. In some implementations, graph data structure querying process 10 may associate each data point of the plurality of data points of the graph data structure with a unique identifier during generation of the graph data structure. In some implementations, each unique identifier may map to a standard classification code. For example and in some implementations, each unique identifier may map to one or more clinical standard codes (e.g., ICD-10-CM, SNOMED, etc.). As known in the art, SNOMED is an international clinical reference terminology designed for use in electronic health records and ICD-10-CM is the International Classification of Diseases, Tenth Revision, Clinical Modification for classifying and coding diagnoses, symptoms, and procedures recorded in conjunction with health care in at least the United States of America. In the example of FIG. 9, the selected data portion (e.g., selected data portion 900) may be associated with a unique identifier (e.g., "55555") which may map to one or more standard classification codes. While a specific numerical code has been provided as an example for the unique identifier, it will be appreciated that any type of code (e.g., alphanumerical codes, non-alphanumerical codes, etc.) may be used within the scope of the present disclosure.

In some implementations and as shown in FIG. 9, graph data structure querying process 10 may receive 202 any number of queries to provide 208 to one or more electronic data sources. In some implementations, selected data points (e.g., selected data point 900) may affect the identification 204 of other data points in response to additional queries. For example, suppose that a user selects the data point (e.g., "bursitis") and that the user provides another query in query bar 502. As discussed above and in some implementations, graph data structure querying process 10 may identify 204 at least one data point from the plurality of data points from the graph data structure based upon, at least in part, the query and the relevance of each data point with the selected data point. For example, suppose that the additional query includes the letters "pain", graph data structure querying process 10 may rank clinically adjacent (e.g., based on clinical relevance) data points and/or data points adjacent to the selected data point from the graph data structure higher than other data points. In this manner, the selected data point (e.g., selected data point 900) may help narrow the list of possible data points for a subsequent query and improve the speed and accuracy of subsequent queries of the graph data structure.

Figure 10:
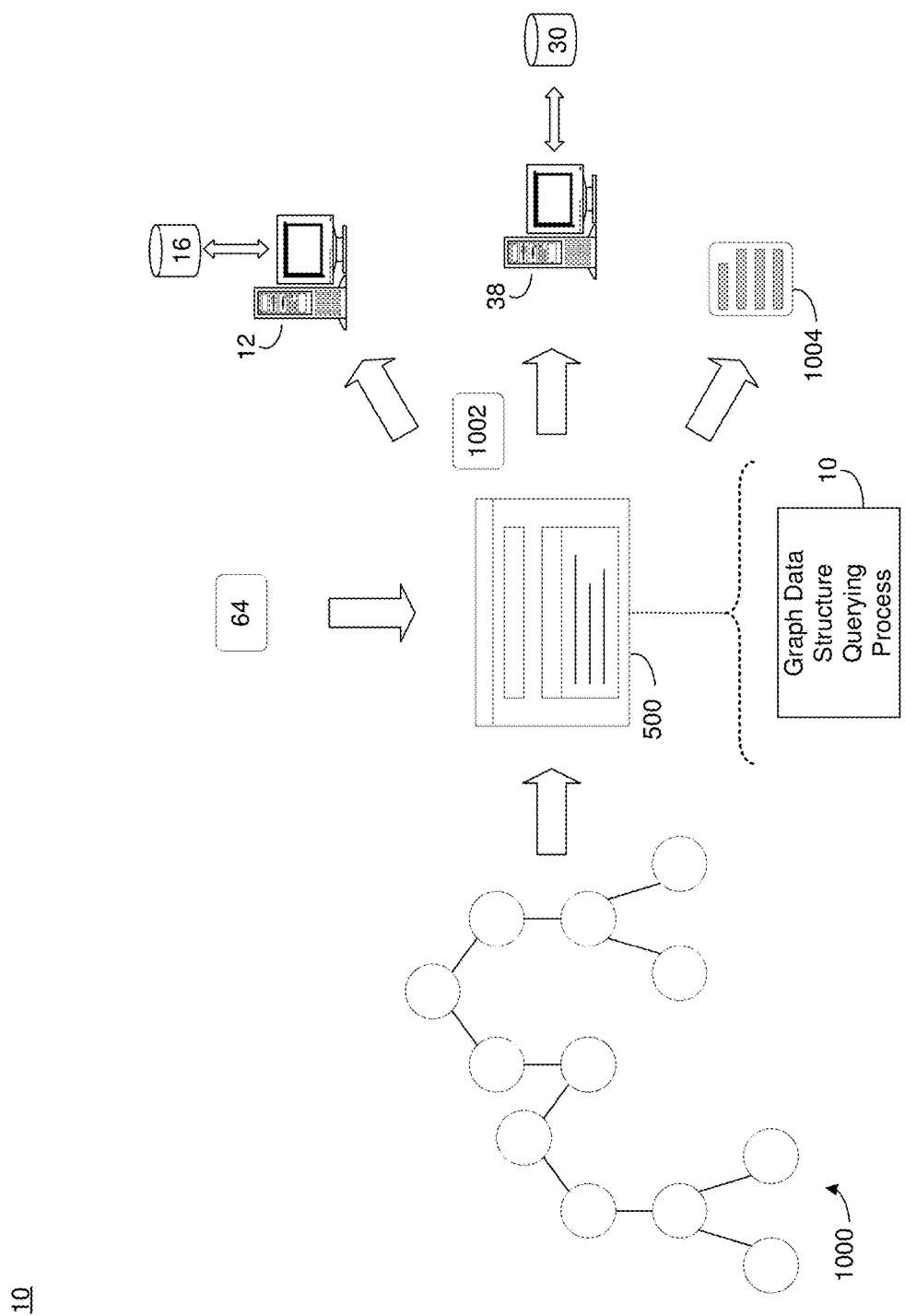
FIG. 10 is a diagrammatic view of a selected data point being provided to one or more electronic data sources according to one implementation of the graph data structure querying process of FIG. 1.

In some implementations, graph data structure querying process 10 may provide 208 the selected data point to one or more electronic data sources. Referring also to FIG. 10 and in some implementations, graph data structure querying process 10 may generate 200 a graph data structure (e.g., graph data structure 1000) with a plurality of data points from one or more electronic forms. Graph data structure querying process 10 may receive 202 a query (e.g., query 64) in a user interface (e.g., user interface 500) for searching the graph data structure (e.g., graph data structure 1000) for at least one data point. In the example of FIG. 10, graph data structure querying process 10 may identify 204 at least one data point from the plurality of data points of the graph data structure (e.g., graph data structure 1000) and may receive 206 a selection, via the user interface, of a data point (e.g., selected data point 1002) from the at least one identified data portion(s). In some implementations, graph data structure querying process 10 may provide 208 the selected data point (e.g., selected data point 1002) to one or more electronic data sources (e.g., computing device 12, computing device 38, and/or electronic form 1004). An electronic data source may generally include any electronic storage device or system. For example, graph data structure querying process 10 may provide the selected data point (e.g., selected data point 1002) to a client computing device (e.g., computing device 12), a network server (e.g., computing device 38), a cloud-computing system, and/or any other accessible computing device.

In a healthcare example, the one or more electronic data sources may be various servers associated with different healthcare entities. For example, electronic form populating process 10 may provide 208 the selected data point to a server associated with a physician providing the query, a server within a medical facility that stores a particular physician's patient's medical files, a server associated with an insurance company, a server associated with a research group, etc. In this manner, electronic form populating process 10 may provide 208 the selected data point to various electronic data sources from a query of a graph data structure generated from one or more electronic forms.

In some implementations, providing 208 the selected data point to one or more data sources includes automatically populating 220 at least a portion of at least one electronic form based upon, at least in part, the selected data point. As discussed above and in some implementations, conventional electronic form applications often require a user to comply with complex documentation requirements. In some implementations, graph data structure querying process 10 may automatically populate 220 at least a portion of at least one electronic form (e.g., electronic form 1004) based upon, at least in part, the selected data point (e.g., selected data point 1002). Returning to the example of FIG. 9, graph data structure querying process 10 may provide 208 the selected data portion (e.g., "bursitis") to an electronic form (e.g., an electronic health record (EHR) associated with a patient) with just a query of the graph data structure (e.g., "in pa kn bu"). In this manner, the process of filling electronic forms with user interfaces may be improved by automatically populating 220 at least a portion of an electronic form using a query made to graph data structure generated with data points from one or more structured data lists, such as electronic forms.

Figure 11:
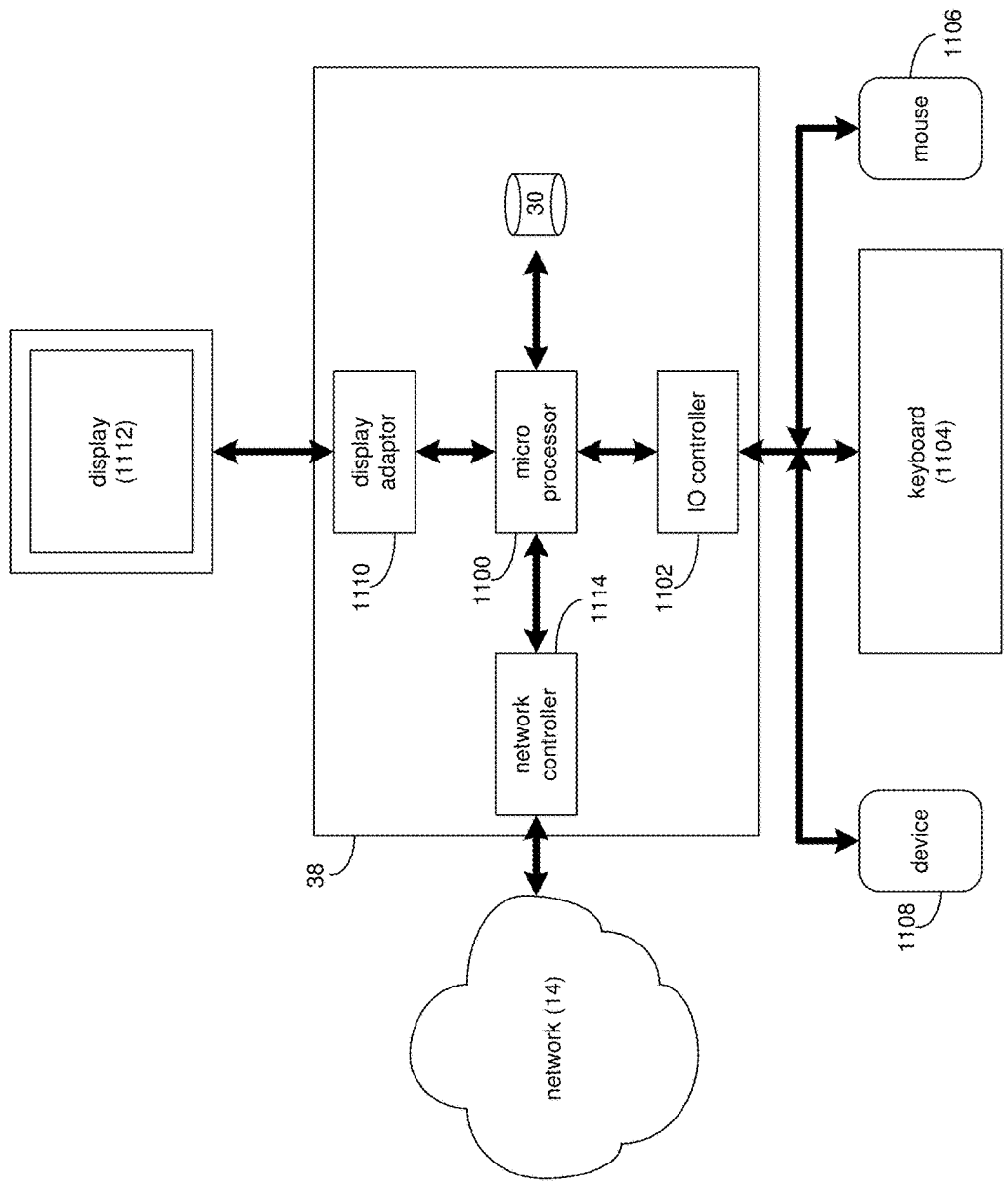
FIG. 11 is an example diagrammatic view of a client electronic device of FIG. 1 according to one or more example implementations of the disclosure.

Referring also to FIG. 11, there is shown a diagrammatic view of client electronic device 38. While client electronic device 38 is shown in this figure, this is for illustrative purposes only and is not intended to be a limitation of this disclosure, as other configurations are possible. For example, any computing device capable of executing, in whole or in part, graph data structure querying process 10 may be substituted for client electronic device 38 within FIG. 11, examples of which may include but are not limited to computing device 12 and/or client electronic devices 40, 42, 44.

Client electronic device 38 may include a processor and/or microprocessor (e.g., microprocessor 1100) configured to, e.g., process data and execute the above-noted code/instruction sets and subroutines. Microprocessor 1100 may be coupled via a storage adaptor (not shown) to the above-noted storage device(s) (e.g., storage device 30). An I/O controller (e.g., I/O controller 1102) may be configured to couple microprocessor 1100 with various devices, such as keyboard 1104, pointing/selecting device (e.g., mouse 1106), custom device, such a microphone (e.g., device 1108), USB ports (not shown), and printer ports (not shown). A display adaptor (e.g., display adaptor 1110) may be configured to couple display 1112 (e.g., CRT or LCD monitor(s)) with microprocessor 1100, while network controller/adaptor 1114 (e.g., an Ethernet adaptor) may be configured to couple microprocessor 1100 to the above-noted network 14 (e.g., the Internet or a local area network).

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    generating, at the computing device, a graph data structure representative of one or more electronic forms, the graph data structure including a plurality of data points, wherein generating the graph data structure representative of the one or more electronic forms includes generating a plurality of nodes and edges within the graph data structure based upon, at least in part, a plurality of sequentially entered data fields from the one or more electronic forms and expected values for the plurality of data fields;
    receiving, via a user interface, a query for the graph data structure;
    identifying, via the user interface, at least one data point from the plurality of data points in the graph data structure based upon, at least in part, the query;
    receiving, via the user interface, a selection of a data point from the identified at least one data point; and
    providing the selected data point to one or more electronic data sources.

2. The computer-implemented method of claim 1, wherein identifying the at least one data point from the plurality of data points in the graph data structure includes one or more of:
    rendering, via the user interface, the at least one data point in a list format; and
    rendering, via the user interface, the at least one data point in a tree format.

3. The computer-implemented method of claim 1, wherein identifying the at least one data point from the plurality of data points in the graph data structure includes:
    determining one or more synonymous queries associated with the query; and
    identifying, via the user interface, the at least one data point from the plurality of data points in the graph data structure based upon, at least in part, the one or more synonymous queries.

4. The computer-implemented method of claim 1, wherein identifying the at least one data point from the plurality of data points in the graph data structure includes:
    adding a data point to the graph data structure based upon, at least in part, the query.

5. The computer-implemented method of claim 1, wherein each data point of the plurality of data points in the graph data structure is associated with a unique identifier that maps to a standard classification code.

6. The computer-implemented method of claim 1, wherein providing the selected data point to one or more data sources includes:
    automatically populating at least a portion of at least one electronic form based upon, at least in part, the selected data point.

7. The computer-implemented method of claim 6, wherein the at least one electronic form includes at least one electronic health record form and the one or more electronic data sources include one or more healthcare databases.

8. A computer program product residing on a non-transitory computer readable medium having a plurality of instructions stored thereon which, when executed by a processor, cause the processor to perform operations comprising:
    generating a graph data structure representative of one or more electronic forms, the graph data structure including a plurality of data points, wherein generating the graph data structure representative of the one or more electronic forms includes generating a plurality of nodes and edges within the graph data structure based upon, at least in part, a plurality of sequentially entered data fields from the one or more electronic forms and expected values for the plurality of data fields;
    receiving, via a user interface, a query for the graph data structure;
    identifying, via the user interface, at least one data point from the plurality of data points in the graph data structure based upon, at least in part, the query;
    receiving, via the user interface, a selection of a data point from the identified at least one data point; and
    providing the selected data point to one or more electronic data sources.

9. The computer program product of claim 8, wherein identifying the at least one data point from the plurality of data points in the graph data structure includes one or more of:
    rendering, via the user interface, the at least one data point in a list format; and
    rendering, via the user interface, the at least one data point in a tree format.

10. The computer program product of claim 8, wherein identifying the at least one data point from the plurality of data points in the graph data structure includes:
    determining one or more synonymous queries associated with the query; and
    identifying, via the user interface, the at least one data point from the plurality of data points in the graph data structure based upon, at least in part, the one or more synonymous queries.

11. The computer program product of claim 8, wherein identifying the at least one data point from the plurality of data points in the graph data structure includes:
    adding a data point to the graph data structure based upon, at least in part, the query.

12. The computer program product of claim 8, wherein each data point of the plurality of data points in the graph data structure is associated with a unique identifier that maps to a standard classification code.

13. The computer program product of claim 8, wherein providing the selected data point to one or more data sources includes:

automatically populating at least a portion of at least one electronic form based upon, at least in part, the selected data point.

14. The computer program product of claim 13, wherein the at least one electronic form includes at least one electronic health record form and the one or more electronic data sources include one or more healthcare databases.

15. A computing system including a processor and memory configured to perform operations comprising:
generating a graph data structure representative of one or more electronic forms, the graph data structure including a plurality of data points, wherein generating the graph data structure representative of the one or more electronic forms includes generating a plurality of nodes and edges within the graph data structure based upon, at least in part, a plurality of sequentially entered data fields from the one or more electronic forms and expected values for the plurality of data fields;
receiving, via a user interface, a query for the graph data structure;
identifying, via the user interface, at least one data point from the plurality of data points in the graph data structure based upon, at least in part, the query;
receiving, via the user interface, a selection of a data point from the identified at least one data point; and
providing the selected data point to one or more electronic data sources.

16. The computing system of claim 15, wherein identifying the at least one data point from the plurality of data points in the graph data structure includes one or more of:
rendering, via the user interface, the at least one data point in a list format; and
rendering, via the user interface, the at least one data point in a tree format.

17. The computing system of claim 15, wherein identifying the at least one data point from the plurality of data points in the graph data structure includes:
determining one or more synonymous queries associated with the query; and
identifying, via the user interface, the at least one data point from the plurality of data points in the graph data structure based upon, at least in part, the one or more synonymous queries.

18. The computing system of claim 15, wherein identifying the at least one data point from the plurality of data points in the graph data structure includes:
adding a data point to the graph data structure based upon, at least in part, the query.

19. The computing system of claim 15, wherein each data point of the plurality of data points in the graph data structure is associated with a unique identifier that maps to a standard classification code.

20. The computing system of claim 15, wherein providing the selected data point to one or more data sources includes:
automatically populating at least a portion of at least one electronic form based upon, at least in part, the selected data point.

21. The computing system of claim 20, wherein the at least one electronic form includes at least one electronic health record form and the one or more electronic data sources include one or more healthcare databases.

* * * * *